(12) United States Patent
Sung et al.

(10) Patent No.: US 9,504,721 B2
(45) Date of Patent: Nov. 29, 2016

(54) BACTERIOPHAGE AND ITS USE FOR PREVENTING PROLIFERATION OF PATHOGENIC BACTERIA

(71) Applicant: CTC BIO, Inc., Seoul (KR)

(72) Inventors: Ki-Hong Sung, Seoul (KR); Dae-Keon Choi, Seoul (KR); Jae-Hoon Kim, Gyeonggi-Do (KR)

(73) Assignee: CTC BIO, INC., Seoul (KR)

( * ) Notice: Subject to any disclaimer, the term of this patent is extended or adjusted under 35 U.S.C. 154(b) by 792 days.

(21) Appl. No.: 13/761,865

(22) Filed: Feb. 7, 2013

(65) Prior Publication Data

US 2013/0323209 A1 Dec. 5, 2013

(30) Foreign Application Priority Data

Jun. 4, 2012 (KR) .................. 10-2012-0059885
Jun. 22, 2012 (KR) .................. 10-2012-0067606
Jun. 25, 2012 (KR) .................. 10-2012-0067811

(51) Int. Cl.
  *C12N 7/00* (2006.01)
  *A61K 35/76* (2015.01)

(52) U.S. Cl.
  CPC .................. *A61K 35/76* (2013.01); *C12N 7/00* (2013.01); *C12N 2795/10121* (2013.01); *C12N 2795/10122* (2013.01)

(58) Field of Classification Search
  None
  See application file for complete search history.

(56) References Cited

PUBLICATIONS

Kim et al. 2012 (Complete Genome Sequence of a Novel Marine Siphovirus, pVp-1, Infecting Vibrio parahaemolyticus; J of Virol 88(10): 7013-7014.*
Kim, J.H. et al., "Complete Genome Sequence of a Novel Marine Siphovirus, pVp-1, Infecting Vibrio parahaemolyticus," Jrl. of Virology, vol. 86, No. 12, pp. 7013-7014 (Jun. 2012).
Kim, J.H. et al., "Isolation and Characterization of a Lytic Myoviridae Bacteriophage PAS-1 with Broad Infectivity in Aeromonas salmonicida," Current Microbiology, 64: 418-426 (2012).
Merino, S. et al "Isolation and characterization of bacteriophage PM2 from Aeromonas hydrophila", FEMS Microbiology Letters, 68 (1990) 239-244.
Seguritan, Victor et al., "Genome Sequences of Two Closely Related Vibrio parahaemolyticus Phages, VP16T and VP16C", Jrl. of Bacteriology, Nov. 2003, vol. 185, No. 21 pp. 6434-6447.

* cited by examiner

*Primary Examiner* — Gary Nickol
*Assistant Examiner* — Mary Lyons
(74) *Attorney, Agent, or Firm* — Mintz Levin Cohn Ferris Glovsky and Popeo, P.C.; Kongsik Kim; Linyu L. Mitra

(57) ABSTRACT

The present invention relates to a novel phage, which is newly isolated and identified, a composition for inhibiting growth of bacteria or killing thereof comprising the same as an active ingredient, and the present invention can be diversely used as a composition for preventing or treating bacterial infectious diseases, a composition for treating ballast water, an antibiotic, an antiseptic, a feed additive and the like.

5 Claims, 16 Drawing Sheets

BACTERIOPHAGE AND ITS USE FOR PREVENTING PROLIFERATION OF PATHOGENIC BACTERIA

CROSS-REFERENCE TO RELATED APPLICATION

The present application claims priority to Korean Patent Application No. 10-2012-0067811 filed in the Republic of Korea on Jun. 25, 2012, Korean Patent Application No. 10-2012-0067606 filed in the Republic of Korea on Jun. 22, 2012, and Korean Patent Application No. 10-2012-0059885 filed in the Republic of Korea on Jun. 4, 2012, the disclosures of which are incorporated herein by reference.

TECHNICAL FIELD

The present disclosure relates to a novel phage, which is newly isolated and identified, a composition for inhibiting growth of bacteria or killing thereof comprising the same as an active ingredient, a composition for preventing or treating bacterial infectious diseases, a composition for treating ballast water, an antibiotic, an antiseptic, and a feed additive.

BACKGROUND ART

The non-motile aeromonad, *Aeromonas salmonicida* that belongs to the family Aeromonadaceae, is the causative agent of bacterial septicemia and furunculosis in a broad variety of fish, and it has caused significant economic losses in worldwide aquaculture (Wiklund T, Dalsgaard I (1998) Occurrence and significance of atypical *Aeromonas salmonicida* in non-salmonid and salmonid fish species: a review. Dis Aquat Organ 32:49-69). Recently, the emergence of antibiotic-resistant *Aeromonas salmonicida* strains in aquaculture has been recognized as great concern including Korea (Kim J H, Hwang S Y, Son J S, Han J E, Jun J W, Shin S P, Choresca C H, Choi Y J, Park Y H, Park S C (2011) Molecular characterization of tetracycline- and quinolone-resistant *Aeromonas salmonicida* isolated in Korea. J Vet Sci 12:41-48). Particularly, although it was reported that in 1951, *Aeromonas salmonicida*, which is most frequently used in fish aquaculture, already acquired resistance to oxytetracycline, it is now used multilaterally. Moreover, the emergence of resistant bacteria caused by the abuse of antibiotics against *Aeromonas salmonicida* and also R-plasmids encoding antibiotic resistant bacteria were also reported. Further, generation of resistance to a second generation antibiotics of 4-quinolones-fluoroquinolones, notably enrofloxacin and sarofloxacin, was also reported. Therefore, alternative control methods are urgently needed.

Theoretically, phage can be used to treat pathogenic bacteria, as an alternative approach to control infectious bacterial disease. In practice, phage has been used as therapeutic or prophylactic agents against several fish and crustacean pathogens (Karunasagar I, Shivu M M, Girisha S K, Krohne G, Karunasagar I (2007) Biocontrol of pathogens in shrimp hatcheries using bacteriophages. Aquaculture 268: 288-292; Kim J H, Gomez D K, Nakai T, Park S C (2010) Isolation and identification of bacteriophages infecting ayu *Plecoglossus altivelis altivelis* specific *Flavobacterium psychrophilum*. Vet Microbiol 140:109-115; Munro J, Oakey J, Bromage E, Owens L (2003) Experimental bacteriophage-mediated virulence in strains of *Vibrio harveyi*. Dis Aquat Org 54:187-194; Nakai T, Park S C (2002) Bacteriophage therapy of infectious diseases in aquaculture. Res Microbiol 153:13-18; Vinod M G, Shivu M M, Umesha K R, Rajeeva B C, Krohne G, Karunasagar I, Karunasagar I (2006) Isolation of *Vibrio harveyi* bacteriophage with a potential for biocontrol of luminous vibriosis in hatchery environments. Aquaculture 255:117-124). Likewise, experimental applications of phages related to control *Aeromonas salmonicida* have been reported using phage HER110 (Imbeault S, Parent S, Lagace M, Uhland C F, Blais J F (2006) Using bacteriophages to prevent furunculosis caused by *Aeromonas salmonicida* in farmed brook trout. J Aquat Anim Health 18:203-214) and phage O, R and B (Verner-Jeffreys D W, Algoet M, Pond M J, Virdee H K, Bagwell N J, Roberts E G (2007) Furunculosis in Atlantic salmon (*Salmo salar* L.) is not readily controllable by bacteriophage therapy. Aquaculture 270:475-484).

However, to date, a number of Aeromonadaceae infectious phages have been isolated and characterized, but according to the VIIIth ICTV report (http://www.ictvdb.org/Ictv/index.htm), most of them were classified into Myoviridae as P1, P2 and T4-like phages. Moreover, recent studies of *Aeromonas* phage have focused on virulent T4-like phage. Other *Aeromonas* phages that belong to Myoviridae but not classified as T4-like phage have not been investigated, with the exception of *Aeromonas* phage φO18P, which has been investigated and classified as P2-like phage and infects *Aeromonas media*, but its infectivity against *Aeromonas salmonicida* has not yet been reported.

The *Vibrio parahaemolyticus* is a gram-negative *bacillus*, which belongs to the family Vibrionaceae, and is known to infect a person, who has an underlying disease in a compromised immune state such as liver diseases, alcoholism and diabetes, eats fish and shellfish infected with raw bacteria or incompletely cooked food, or has a wound that is exposed in contaminated seawater. In many countries including Korea and Japan, its occurrence is continuously growing every year due to habits of eating raw fish and shellfish, and is known as a huge problem due to its high collective occurrence. Recently, according to the increase of eating raw fish and shellfish in many countries in the West, outbreaks of disease caused by the bacteria infection is spreading all over the US, Europe, and across the world. This infectious disease is known to be closely related to particularly oyster, and because these bacterias actively reproduce when water temperature rises, sale and distribution of oyster are banned every summer, particularly during June-September when they are the most prevalent. Particularly, extra precaution is demanded due to the increase of group meals and the like which could lead to a pandemic.

The motile *Aeromonas*, *Aeromonas hydrophila* belonging to the family Aeromonadaceae, infects a broad variety of fish and causes septicemia, bleeding, an ulcer and the like, and mass mortality, resulted therefrom, cause significant economic losses. Particularly, in domestic aquaculture farms, *Aeromonas hydrophila* disease can become strongly infectious due to breeding performed in very crowded and limited spaces. Most representative examples of such aquarium fish are, carp and goldfish, which are severely damaged by *Aeromonas hydrophila* in fish farming markets all over Jincheon, Chungcheongbuk-do.

The *Aeromonas hydrophila*, which is an underwater resident flora, is prevented by treating with antibiotics thereto in many cases. Consequently, most of the *Aeromonas hydrophila* show resistance against antibiotics, and the remaining antibiotics becomes a threat to national health and also damages caused by the occurrence of resistant bacteria becomes more severe.

On the other hand, bacteriophage is a virus that specifically infects bacteria, and was founded by Twort, an English bacteriologist, in 1915, during his research on the phenomenon that *micrococcus* colony when decomposed turns the bacterial transparent. Also in 1917, a French bacteriologist d'Herelle found out that there was something that decomposes *Shigella disentriae* in filtrate of feces of a patient with dysentery, and continued to study to identify the material, leading to the finding of bacteriophage which means "eating bacteria". Therapeutics using phage, have been continuously studied only in East Europe and Soviet after the development of antibiotics. However, recently, because multidrug-resistant pathogenic bacteria and super bacteria resulted from over-use and/or mis-use of antibiotics have been frequently reported, and many problems of the conventional antibiotics have emerged, it has gained attention as an alternative for antibiotics. Moreover, bacteriophage has advantages in terms of short development time and low development costs, bacteria selectivity, sustainability, side effects and the like in comparison to antibiotics.

SUMMARY OF THE DISCLOSURE

The present disclosure is designed to solve the problems of the prior art, and therefore it is an object of the present disclosure to provide a newly isolated phage having a bacteriolytic activity to *Aeromonas salmonicida*, a composition for inhibiting growth of *Aeromonas salmonicida* or killing thereof comprising the same, a composition for preventing or treating *Aeromonas salmonicida* infectious disease, an antibiotic, an antiseptic, and a feed additive for fish and crustacean.

In addition, it is another object of the present disclosure to provide a newly isolated bacteriophage having a bacteriolytic activity to *Vibrio parahaemolyticus*, a composition for inhibiting growth of *Vibrio parahaemolyticus* or killing thereof comprising the same, a composition for treating ballast water, a pharmaceutical composition for preventing or treating *Vibrio parahaemolyticus* infectious disease, an antibiotic, an antiseptic, and a feed additive for fish and shellfish.

In addition, it is further another object of the present disclosure to provide a newly isolated bacteriophage having a bacteriolytic activity to *Aeromonas hydrophila*, a composition for inhibiting growth of *Aeromonas hydrophila* or killing thereof comprising the same, a pharmaceutical composition for preventing or treating *Aeromonas hydrophila* infectious disease, an antibiotic, an antiseptic, and a feed additive for fish.

BRIEF DESCRIPTION OF DRAWINGS

Other objects and aspects of the present disclosure will become apparent from the following descriptions of the embodiments with reference to the accompanying drawings in which.

DETAILED DESCRIPTION

Figure 1:
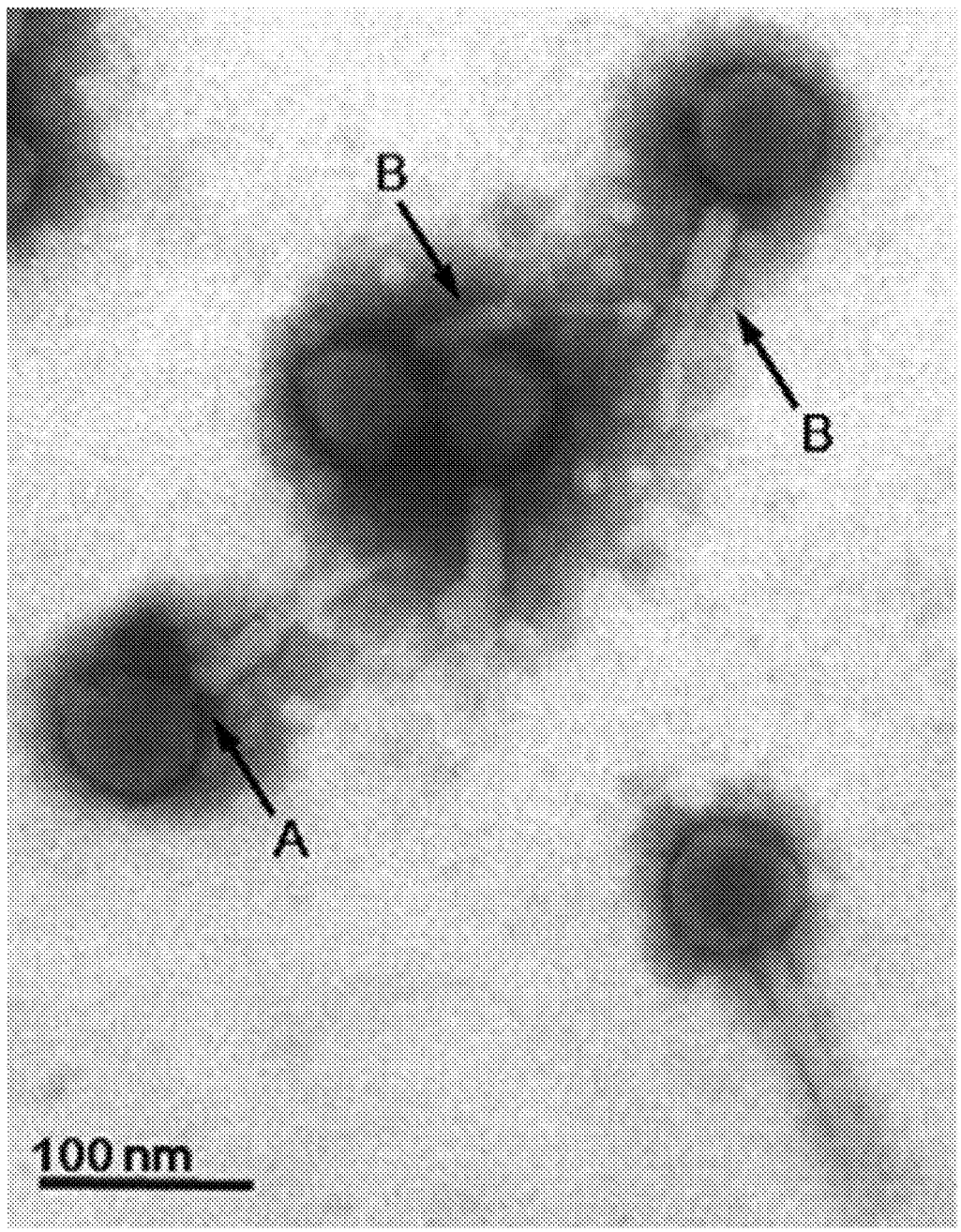
FIG. 1 is the result of observing the negatively stained ASP-1 virion using an electron microscope. Arrows A and B indicate the neck and the contracted tail, respectively.

[Novel Phage ASP-1 and its Use for Inhibiting Growth of *Aeromonas salmonicida*]

As one embodiment, the present invention relates to a phage having a specific killing activity to *Aeromonas salmonicida*.

Specifically, it is characterized that the phage has a specific killing activity to *Aeromonas salmonicida* subsp. *salmonicida*, *Aeromonas salmonicida* subsp. *achromogenes* and *Aeromonas salmonicida* subsp. *masoucida*, morphologically belongs to the family Myoviridae, the order Caudovirales and morphotype A1, and its RNA polymerase, DNA polymerase, large subunit terminase, tail fiber, muramidase, head portal protein and one hypothetical protein gene have nucleotide sequence accession numbers of JF342689, JF342683, JF342686, JF342690, JF342687, JF342688 and JF342684, respectively.

It is characterized that the phage is a phage of accession number: KCTC 12127BP.

The present inventors collected sediment samples from rainbow trout culture farms in Korea, and a phage having a killing activity to *Aeromonas salmonicida* and the said characteristics was isolated and identified. The phage was named ASP-1, and was deposited in Korean collection for type culture (125 Gwahak-ro, Yuseong-gu, Daejeon 305-806, Republic of Korea) under accession number of KCTC 12127BP on Feb. 3, 2012.

The present inventors collected samples from rainbow trout culture farms in Korea, and isolated a phage (hereinafter, called ASP-1), which uses *Aeromonas salmonicida* subsp. *salmonicida* AS01 as a host and bacteriolyzes thereof, from the samples, and it was confirmed that the ASP-1 had the bacteriolytic activity by forming plaques to *Aeromonas salmonicida* subsp. *achromogenes*, *Aeromonas salmonicida* subsp. *masoucida* and *Aeromonas salmonicida* subsp. *salmonicida*. In addition, it was confirmed that, in the bacteriolyzed *Aeromonas salmonicida* subsp. *Salmonicida*, there were also multi-drug resistant strains including antibiotics resistance (AS09, 10, 11, 12, 13, 14 and 15). Particularly, the phage showed the highest EOP value to the multi-drug resistant strain, *Aeromonas salmonicida* subsp. *salmonicida* AS09 (see Table 1).

Further, as a result of morphologically observing the ASP-1 through an electron microscope, it was found that it belongs to the family Myoviridae, the order Caudovirales and morphotype A1.

Further, as a result of analyzing ASP-1 genome, it was confirmed that it is composed of double-strand DNA (dsDNA) and its genome size is about 48 kb, and as a result of analyzing four partial ORF sequences of phage-related proteins (RNA polymerase, DNA polymerase, large subunit terminase and tail fiber) and three complete ORF sequences (muramidase, head portal protein and hypothetical protein), it was confirmed that accession number of each nucleotide sequence is JF342689, JF342683, JF342686, JF342690, JF342687, JF342688 and JF342684. Moreover, it was found that the ASP-1 is a novel phage because the entire ASP-1 genome did not show apparent homology with other phages.

As another embodiment, the present invention relates to a composition for inhibiting growth of *Aeromonas salmonicida* or killing thereof comprising the phage or its culture as an active ingredient, or a method for inhibiting growth of *Aeromonas salmonicida* or killing thereof by treating the phage or its culture.

As further another embodiment, the present invention relates to an antibiotic, an antiseptic and a feed additive for fish and crustacean, which comprises the phage or its culture, or a composition for inhibiting growth of *Aeromonas salmonicida* comprising the phage or its culture as an active ingredient.

The composition for inhibiting growth of *Aeromonas salmonicida* or killing thereof, the antibiotic, the antiseptic and the feed additive according to the present invention showed very high specificity to *Aeromonas salmonicida*, compared with the existing materials. Accordingly, they have excellent effects of killing only a specific pathogen without the side effect of killing friendly bacteria, and also killing multi-drug resistant pathogen; and they have longer product life than the existing products because they do not induce tolerance or resistance against pathogen.

The phage ASP-1 according to the present invention can be cultured by common phage culture methods in large quantities. As a culture medium, a medium composed of carbon source, nitrogen source, vitamin and mineral can be used. For example, NB (nutrient broth), TSB (tryptic soy broth) liquid medium, or TSA (tryptic soy agar) solid medium and the like can be used. The culture can be conducted under common culture conditions. In order to remove the culture medium in the culture solution and harvest only concentrated cells, centrifugation or filtration process can be used, and this step can be conducted depending on the need of a person having ordinary skill in the art. The concentrated cells can be preserved by freezing or freeze-drying so as not to lose its activity.

Preferably, the *Aeromonas salmonicida* is at least one selected from the group consisting of *Aeromonas salmonicida* subsp. *salmonicida*, *Aeromonas salmonicida* subsp. *achromogenes* and *Aeromonas salmonicida* subsp. *masoucida*. More preferably, the *Aeromonas salmonicida* subsp. *salmonicida* is *Aeromonas salmonicida* subsp. *salmonicida* AS01, AS02, AS04, AS05, AS06, AS07, AS08, AS09, AS10, AS11, AS12, AS13, AS14, AS15 or ATCC 33658, the *Aeromonas salmonicida* subsp. *achromogenes* is *Aeromonas salmonicida* subsp. *achromogenes* AS03, and the *Aeromonas salmonicida* subsp. *masoucida* is *Aeromonas salmonicida* subsp. *masoucida* ATCC 27013.

Further, preferably, the *Aeromonas salmonicida* is a multi-drug resistant strain.

The composition for inhibiting growth of *Aeromonas salmonicida* or killing thereof, the antibiotic, the antiseptic and the feed additive for fish and crustacean can further comprise an acceptable carrier, and can be formulated with the carrier. The acceptable carrier refers to a carrier not stimulating an organism and not suppressing biological activity and characteristics. It can be manufactured in the form of water-dispersible agent, water-dispersible powder, water-dispersible solution, liquid, aqueous solution, water-soluble powder or capsule by a surfactant or an extender and the like for the purpose of stable formulation suitable for real package. As one example of the surfactant, one selected from the group consisting of: sodium salt or calcium salt of sulfonate compound such as alkyl($C_8$~$C_{12}$) arylsulfonate, dialkyl($C_3$~$C_6$)arylsulfonate, dialkyl($C_8$~$C_{12}$)sulfosuccinate, ligninsulfonate, naphthalenesulfonatecondensate, naphthalenesulfonateformalincondensate, alkyl($C_8$~$C_{12}$) naphthalenesulfonateformalincondensate and polyoxyethylenealkyl($C_8$~$C_{12}$)phenylsulfonate; sodium salt or calcium salt of sulfate compound such as alkyl($C_8$~$C_{12}$)sulfate, alkyl ($C_8$~$C_{12}$)arylsulfate, polyoxyethylenealkyl($C_8$~$C_{12}$)sulfate and polyoxyethylenealkyl($C_8$~$C_{12}$)phenylsulfate; sodium salt or calcium salt of succinate compound such as polyoxyalkylene succinate; anionic surfactant such as sodium benzoate, alkylcarboxylate and the like; nonionic surfactant such as polyoxyethylenealkyl($C_{12}$~$C_{18}$)ether, polyoxyethylenealkyl($C_8$~$C_{12}$)phenylether, polyoxyethylenealkyl ($C_8$~$C_{12}$)phenylpolymer and ethyleneoxide propyleneoxide copolymer; polycarboxylate; Triton 100; and Tween 80 can be used alone or in combination of two or more, and it will be easily understood to a person having ordinary skill in the art that surfactants other than the said surfactants also can be used. As the extender, bentonite, talc, clay, kaolin, calcium carbonate, silica sand, pumice stone, diatomite, acid clay, zeolite, pearlite, white carbon, ammonium sulfate, urea, glucose, dextrin, bean flour, rice, wheat, yellow soil, glucose and starch, water and the like can be used alone or in combination of two or more, and it will be easily understood to a person having ordinary skill in the art that extenders other than the said extenders also can be used.

The 'antibiotic' includes a preservative, a disinfectant and an antimicrobial.

The feed additive can be added to a feed for fish or crustacean.

Or, when manufacturing a feed, the ASP-1 or its culture can be directly added to the feed, but not mixed thereto after manufactured separately in the form of a feed additive.

As further another embodiment, the present invention relates to a composition for preventing or treating *Aeromonas salmonicida* infectious disease comprising the phage or its culture as an active ingredient, or a method for preventing or treating the *Aeromonas salmonicida* infectious disease using the same.

As described above, the phage according to the present invention has a specific killing activity to the *Aeromonas salmonicida*, thereby showing an effect on preventing or treating various diseases caused by *Aeromonas salmonicida* infection.

Preferably, the *Aeromonas salmonicida* infectious disease is bacterial septicemia or furunculosis, but not limited thereto.

The 'preventing or treating' includes preventing, inhibiting and relieving the *Aeromonas salmonicida* infectious disease.

The composition of the present invention can be administered into an animal in the form of a pharmaceutical formulation, or by feeding after mixing thereof into a feed or drinking water.

The composition of the present invention can be administered through a variety of routes such as an oral route or a parenteral route only if the composition can reach a target tissue, and specifically, it can be administered through general methods such as oral, rectal, topical, intravenous, intrapenitoneal, intra-muscular, intra-arterial, transdermal, intranasal, inhalation.

The method of the present invention for preventing or treating includes administrating the composition of the present invention with a pharmaceutically effective dose. It is obvious to a person having ordinary skill in the art that the suitable daily dose can be decided by a doctor in charge within the scope of proper medical judgment. It is preferred that the therapeutically effective dose for a specific subject may be differently determined according to various factors or pseudo-factors well-known in the medical field, for example, the kind and extent of reaction to be achieved, age, body weight, general health conditions, gender and diet of the subject, administration time, administration route, distribution ratio of composition, treatment duration and drug used together or simultaneously with the specific compositions.

[Novel Phage PVP-1 and its Use for Inhibiting Growth of *Vibrio parahaemolyticus*]

As one embodiment, the present invention relates to a phage having a specific killing activity to *Vibrio parahaemolyticus*.

Specifically, the phage is characterized by morphologically belonging to the family siphovirida and the order Caudovirales, and having accession number: KCTC 12130BP.

The present inventors collected sediment samples from seawater of oyster farm in The southern sea of Korea, and isolated and identified a phage having a killing activity to *Vibrio parahaemolyticus*. The phage was named PVP-1, and was deposited in Korean collection for type culture (125 Gwahak-ro, Yuseong-gu, Daejeon 305-806, Republic of Korea) under accession number of KCTC 12130BP on Feb. 3, 2012.

The present inventors isolated a phage (hereinafter, called PVP-1), which uses *Vibrio parahaemolyticus* of ATCC 33844 as a host and bacteriolyzes thereof, and it was confirmed that the PVP-1 had the bacteriolytic activity by forming plaques to *Vibrio parahaemolyticus*.

Further, as a result of morphologically observing the PVP-1 through an electron microscope, it was found that it belongs to the family siphoviridae and the order Caudovirales.

Further, as a result of analyzing PVP-1 genome, it was confirmed that it is composed of double-helix DNA (ds-DNA) and its genome size is about 100 kb, and it was found that the PVP-1 is the first bacteriophage, which has infectivity to *Vibrio parahaemolyticus* and belongs to the family siphoviridae, because the entire PVP-1 genome did not show homology with other phages.

The phage PVP-1 according to the present invention can be cultured by common phage culture methods in large quantities. As a culture medium, a medium composed of carbon source, nitrogen source, vitamin and mineral can be used. For example, NB (nutrient broth), TSB (tryptic soy broth) liquid medium, or TSA (tryptic soy agar) solid medium and the like can be used. The culture can be conducted under common culture conditions. In order to remove the culture medium in the culture solution and harvest only concentrated cells, centrifugation or filtration process can be used, and this step can be conducted depending on the need of a person having ordinary skill in the art. The concentrated cells can be preserved by freezing or freeze-drying so as not to lose its activity.

The PVP-1 shows sensitivity to *Vibrio parahaemolyticus*.

Preferably, the *Vibrio parahaemolyticus* is *Vibrio parahaemolyticus* ATCC27969, ATCC33844, ATCC17802, VP01, VP02, VP03, VP04, VP05, VP06, VP07, VP08, VP09, VP10, VP11, VP13, VP14, VP17, VP18, VP20, VP21, VP22, VP23, VP24, VP25, VP26, or VP27.

Preferably, the *Vibrio parahaemolyticus* is a multi-drug resistant strain.

Accordingly, as another embodiment, the present invention relates to a composition for inhibiting growth of *Vibrio parahaemolyticus* or killing thereof comprising the phage PVP-1 or its culture as an active ingredient, or a method for inhibiting growth of *Vibrio parahaemolyticus* or killing thereof by treating the same.

As further another embodiment, the present invention relates to the phage PVP-1 or its culture, or an antibiotic, an antiseptic and a feed additive for fish and shellfish comprising thereof an active ingredient. Preferably, it relates to the phage PVP-1 or its culture, or an antibiotic, an antiseptic and a feed additive for fish and shellfish comprising thereof an active ingredient for inhibiting growth of *Vibrio parahaemolyticus* or killing thereof.

The composition for inhibiting growth of *Vibrio parahaemolyticus* or killing thereof, the antibiotic, the antiseptic and the feed additive according to the present invention showed very high specificity to *Vibrio parahaemolyticus*, compared with the existing materials. Accordingly, they have excellent effects of killing only *Vibrio parahaemolyticus* without side effect of killing friendly bacteria, and also killing antibiotic resistant bacteria and a multi-drug resistant pathogen; and they have longer product life than the existing products because they do not induce tolerance or resistance against pathogen.

In the specification of the present invention, 'antibiotic' means a preservative, a disinfectant and an antimicrobial.

The feed additive can be added to a feed for fish or shellfish.

Or, when manufacturing a feed, the PVP-1 or its culture can be directly added to the feed, but not mixed thereto after manufactured separately in the form of a feed additive.

The fish and shellfish may include oyster, clam, crab, shrimp or fish, but not limited thereto.

As further another embodiment, the present invention relates to the phage PVP-1 or its culture, or a composition for treating ballast water comprising thereof as an active ingredient; and a method for biologically treating ballast water by using the same. Preferably, it relates to the phage PVP-1 or its culture, or a composition for treating ballast water comprising thereof as an active ingredient in order to inhibit growth of *Vibrio parahaemolyticus* or kill thereof; and a method for biologically treating ballast water by using the same.

The composition for treating ballast water can kill *Vibrio parahaemolyticus*, which may be in the ballast water, or inhibits growth thereof.

The ballast water refers to sea water taken up in a tank at the bottom of a ship and released to keep its balance so as not to incline to one side when cargo is being unloaded or loaded, or to prevent a screw propeller from rising above the surface of the water which makes sailing impossible.

In this specification, the 'ballast water' indicates ballast water stored in a ballast water tank and also water pumped up through a pump to be stored in the ballast water tank.

In the specification of the present invention, the 'ship' means any kind of ship sailing in the ocean and includes a submarine, a floating ship, a floating platform, a floating storage equipment, and floating equipment for storing or loading and unloading products.

The composition for inhibiting growth of *Vibrio parahaemolyticus* or killing thereof, the composition for treating ballast water, the antibiotic, the antiseptic and the feed additive for fish and shellfish can be manufactured in the liquid form such as solution, suspension, emulsion, but it also can be manufactured in the solid form based on a dried phage such as powder, granule, tablet or capsule.

The composition for inhibiting growth of *Vibrio parahaemolyticus* or killing thereof, the composition for treating ballast water, the antibiotic, the antiseptic and the feed additive for fish and shellfish can further comprise an acceptable carrier, and can be formulated with the carrier. The acceptable carrier refers to a carrier not stimulating an organism and not suppressing biological activity and characteristics. It can be manufactured in the form of water-dispersible agent, water-dispersible powder, water-dispersible solution, liquid, aqueous solution, water-soluble powder or capsule by a surfactant or an extender and the like for the purpose of stable formulation suitable for real package. As one example of the surfactant, one selected from the group consisting of: sodium salt or calcium salt of sulfonate compound such as alkyl($C_8$~$C_{12}$)arylsulfonate, dialkyl ($C_3$~$C_6$)arylsulfonate, dialkyl($C_8$~$C_{12}$)sulfosuccinate,ligninsulfonate, naphthalenesulfonatecondensate, naphthalenesulfonateformalincondensate, alkyl($C_8$~$C_{12}$) naphthalenesulfonateformalincondensate and polyoxyethylenealkyl($C_8$~$C_{12}$)phenylsulfonate; sodium salt or calcium salt of sulfate compound such as alkyl($C_8$~$C_{12}$) sulfate, alkyl($C_8$~$C_{12}$)arylsulfate, polyoxyethylenealkyl ($C_8$~$C_{12}$)sulfate and polyoxyethylenealkyl($C_8$~$C_{12}$)phenylsulfate; sodium salt or calcium salt of succinate compound such as polyoxyalkylene succinate; anionic surfactant such as sodium benzoate, alkylcarboxylate and the like; nonionic surfactant such as polyoxyethylenealkyl($C_{12}$~$C_{18}$)ether, polyoxyethylenealkyl($C_8$~$C_{12}$)phenylether, polyoxyethylenealkyl($C_8$~$C_{12}$)phenylpolymer and ethyleneoxide propyleneoxide copolymer; polycarboxylate; Triton 100; and Tween 80 can be used alone or in combination of two or more, and it will be easily understood to a person having ordinary skill in the art that surfactants other than the said surfactants also can be used. As the extender, bentonite, talc, clay, kaolin, calcium carbonate, silica sand, pumice stone, diatomite, acid clay, zeolite, pearlite, white carbon, ammonium sulfate, urea, glucose, dextrin, bean flour, rice, wheat, yellow soil, glucose and starch, water and the like can be used alone or in combination of two or more, and it will be easily understood to a person having ordinary skill in the art that extenders other than the said extenders also can be used.

It will be easily understood to a person having ordinary skill in the art that the concentration of the phage or the content of the dried phage in the composition for inhibiting growth of *Vibrio parahaemolyticus* or killing thereof, the composition for treating ballast water, the antibiotic, the antiseptic and the feed additive for fish and shellfish can be optionally controlled according to purpose of use. For example, in the case of the composition for treating ballast water, it can be variously controlled by factors such as the amount of ballast water, the number of *Vibrio parahaemolyticus* per unit volume and the content of the PVP-1 in the corresponding composition (or antibiotic, antiseptic, or feed additive for fish and shellfish), and a method for formulating or administrating the composition.

The composition for inhibiting growth of *Vibrio parahaemolyticus* or killing thereof, the composition for treating ballast water, the antibiotic, the antiseptic and the feed additive for fish and shellfish may further comprise an active bacteriophage other than the PVP-1, and the active bacteriophage may preferably be a phage having the bacteriolytic activity to *Vibrio parahaemolyticus*, but not limited thereto, and it also includes a phage having the bacteriolytic activity to other bacteria.

Further, when treating the composition for inhibiting growth of *Vibrio parahaemolyticus* or killing thereof, the composition for treating ballast water, the antibiotic, the antiseptic and the feed additive for fish and shellfish, general methods, which were used for inhibiting growth of *Vibrio parahaemolyticus* or killing thereof in the past, can be used in combination.

As further another embodiment, the present invention relates to a pharmaceutical composition for preventing or treating *Vibrio parahaemolyticus* infectious disease comprising the phage or its culture as an active ingredient, or a method for preventing or treating the *Vibrio parahaemolyticus* infectious disease by using the same.

As described above, the phage according to the present invention having the specific killing activity to *Vibrio parahaemolyticus* shows an effect on preventing or treating various diseases caused by *Vibrio parahaemolyticus* infection. Preferably, the *Vibrio parahaemolyticus* infectious disease is gastroenteritis, food poisoning or infection of wound, but not limited thereto. Further, the *Vibrio parahaemolyticus* infectious disease includes symptoms expressed from the diseases, for example, vomit, stomachache, fever, chill or watery diarrhea.

The 'preventing or treating' includes preventing, inhibiting and relieving the *Vibrio parahaemolyticus* infectious disease.

The composition of the present invention can be administered into an animal in the form of a pharmaceutical formulation, or by feeding after mixing thereof into a feed or drinking water.

The composition of the present invention can be administered through a variety of routes such as an oral route or a parenteral route only if the composition can reach a target tissue, and specifically, it can be administered through general methods such as oral, rectal, topical, intravenous, intrapenitoneal, intra-muscular, intra-arterial, transdermal, intranasal, inhalation.

The method of the present invention for preventing or treating includes administrating the composition of the present invention with a pharmaceutically effective dose. It is obvious to a person having ordinary skill in the art that the suitable daily dose can be decided by a doctor in charge within the scope of proper medical judgment. It is preferred that the therapeutically effective dose for a specific subject may be differently determined according to various factors or pseudo-factors well-known in the medical field, for example, the kind and extent of reaction to be achieved, age, body weight, general health conditions, gender and diet of the subject, administration time, administration route, distribution ratio of composition, treatment duration and drug used together or simultaneously with the specific compositions.

[Novel Phage PAH1-C and PAH6-C and their Uses for Inhibiting Growth of *Aeromonas hydrophila*]

As one embodiment, the present invention relates to a bacteriophage having a specific killing activity to *Aeromonas hydrophila*, which is characterized in that it morphologically belongs to the family Myoviridae and the order Caudovirales, and is a bacteriophage having accession number: KCTC 12128BP or a bacteriophage having accession number: KCTC 12129BP.

The present inventors isolated and identified phages having killing activity to *Aeromonas hydrophila*, and the phages were named PAH1-C and PAH6-C, and were deposited in Korean collection for type culture (125 Gwahak-ro, Yuseong-gu, Daejeon 305-806, Republic of Korea) under accession number of KCTC 12128BP and accession number of KCTC 12129BP, respectively, at Feb. 3, 2012.

The present inventors collected sediment samples from Seoam stream, Haseong, and isolated a phage (hereinafter, called PAH1-C), which uses *Aeromonas hydrophila* JUNAH as a host and bacteriolyzes thereof, from the sample; and isolated a phage (hereinafter, called PAH6-C), which bacteriolyzes *Aeromonas hydrophila* JUNAH, from samples collected from Nanji water replacement center. It was confirmed that the PAH1-C and the PAH6-C had the bacteriolytic activity by forming plaques to *Aeromonas hydrophila*.

Further, as a result of morphologically observing the PAH1-C and the PAH6-C through an electron microscope, it was found that it belongs to the family Myoviridae and the order Caudovirales.

Further, as a result of analyzing genomes of the PAH1-C and the PAH6-C, it was confirmed that each of them is composed of double-helix DNA (dsDNA) has genome size of about 50 kb, and it was found that the PAH1-C and the PAH6-C1 are novel bacteriophages, because the entire genomes of the PAH1-C and the PAH6-C1 did not show obvious homology with other phages, and therefore, the genome size of the PAH1-C and the PAH6-C1 are largely different from the bacteriophages, which are known to have infectivity to *Aeromonas hydrophila* up to now.

In the specification of the present invention, the 'PAH1-C or PAH6-C' includes phage culture as well as the phage itself.

The PAH1-C phage or the PAH6-C phage according to the present invention can be cultured by common phage culture methods in large quantities. As a culture medium, a medium composed of carbon source, nitrogen source, vitamin and mineral can be used. For example, NB (nutrient broth), TSB (tryptic soy broth) liquid medium, or TSA (tryptic soy agar) solid medium and the like can be used. The culture can be conducted under common culture conditions. In order to remove the culture medium in the culture solution and harvest only concentrated cells, centrifugation or filtration process can be used, and this step can be conducted depending on the need of a person having ordinary skill in the art. The concentrated cells can be preserved by freezing or freeze-drying so as not to lose its activity.

The PAH1-C and the PAH6-C show sensitivity to *Aeromonas hydrophila*.

More specifically, the PAH1-C shows the sensitivity to *Aeromonas hydrophila AH*1, AH6, AH9, AH16, AK1 and AK9, and the PAH6-C shows the sensitivity to *Aeromonas hydrophila* AH7, AH16, AK1 and AK9.

Further, preferably, the *Aeromonas hydrophila* is an antibiotic resistant strain or a multi-drug resistant strain.

Accordingly, as another embodiment, the present invention relates to a composition for inhibiting growth of *Aeromonas hydrophila* or killing thereof comprising the PAH1-C or the PAH6-C as an active ingredient, or a method for inhibiting growth of *Aeromonas hydrophila* or killing thereof by treating the same.

As further another embodiment, the present invention relates to the PAH1-C or the PAH6-C, or an antibiotic, an antiseptic and a feed additive for fish comprising thereof an active ingredient. Preferably, it relates to the phage PAH1-C or PAH6-C, or an antibiotic, an antiseptic and a feed additive for fish comprising thereof an active ingredient for inhibiting growth of *Aeromonas hydrophila* or killing thereof.

In the specification of the present invention, the 'antibiotic' means a preservative, a disinfectant and an antimicrobial.

The feed additive can be added to a feed for fish.

Or, when manufacturing a feed, the PAH1-C or the PAH6-C can be directly added to the feed, not mixed thereto after manufactured separately in the form of a feed additive.

The fish may include carp, cichlid, bass, cod, crucian carp, salmon, stingfish, loach, catfish or goby, but not limited thereto.

The composition for inhibiting growth of *Aeromonas hydrophila* or killing thereof, the antibiotic, the antiseptic and the feed additive according to the present invention showed very high specificity to *Aeromonas hydrophila*, compared with the existing materials. Accordingly, they have excellent effects of killing only a specific pathogen without side effect of killing friendly bacteria, and also killing multi-drug resistant pathogen; and they have longer product life than the existing products because they do not induce tolerance or resistance against pathogen.

The composition for inhibiting growth of *Aeromonas hydrophila* or killing thereof, the antibiotic, the antiseptic and the feed additive can be manufactured in the liquid form such as solution, suspension, emulsion, but it also can be manufactured in the solid form based on a dried phage such as powder, granule, tablet or capsule.

The composition for inhibiting growth of *Aeromonas hydrophila* or killing thereof, the antibiotic, the antiseptic and the feed additive can further comprise an acceptable carrier, and can be formulated with the carrier. The acceptable carrier refers to a carrier not stimulating an organism and not suppressing biological activity and characteristics. It can be manufactured in the form of water-dispersible agent, water-dispersible powder, water-dispersible solution, liquid, aqueous solution, water-soluble powder or capsule by a surfactant or an extender and the like for the purpose of stable formulation suitable for real package. As one example of the surfactant, one selected from the group consisting of: sodium salt or calcium salt of sulfonate compound such as alkyl($C_8$~$C_{12}$) arylsulfonate, dialkyl($C_3$~$C_6$)arylsulfonate, dialkyl($C_8$~$C_{12}$)sulfosuccinate, ligninsulfonate, naphthalenesulfonatecondensate, naphthalenesulfonateformalincondensate, alkyl($C_8$~$C_{12}$)naphthalenesulfonateformalincondensate and polyoxyethylenealkyl($C_8$~$C_{12}$)phenylsulfonate; sodium salt or calcium salt of sulfate compound such as alkyl($C_8$~$C_{12}$)sulfate, alkyl($C_8$~$C_{12}$)arylsulfate, polyoxyethylenealkyl($C_8$~$C_{12}$)sulfate and polyoxyethylenealkyl ($C_8$~$C_{12}$)phenylsulfate; sodium salt or calcium salt of succinate compound such as polyoxyalkylene succinate; anionic surfactant such as sodium benzoate, alkylcarboxylate and the like; nonionic surfactant such as polyoxyethylenealkyl($C_{12}$~$C_{18}$)ether, polyoxyethylenealkyl($C_8$~$C_{12}$) phenylether, polyoxyethylenealkyl($C_8$~$C_{12}$)phenylpolymer and ethyleneoxide propyleneoxide copolymer; polycarboxylate; Triton 100; and Tween 80 can be used alone or in combination of two or more, and it will be easily understood to a person having ordinary skill in the art that surfactants other than the said surfactants also can be used. As the extender, bentonite, talc, clay, kaolin, calcium carbonate, silica sand, pumice stone, diatomite, acid clay, zeolite, pearlite, white carbon, ammonium sulfate, urea, glucose, dextrin, bean flour, rice, wheat, yellow soil, glucose and starch, water and the like can be used alone or in combination of two or more, and it will be easily understood to a person having ordinary skill in the art that extenders other than the said extenders also can be used.

It will be easily understood to a person having ordinary skill in the art that the concentration of the phage or the content of the dried phage in the composition for inhibiting growth of *Aeromonas hydrophila* or killing thereof, the antibiotic, the antiseptic and the feed additive can be optionally controlled according to purpose of use.

The composition for inhibiting growth of *Aeromonas hydrophila* or killing thereof, the antibiotic, the antiseptic and the feed additive may comprise the PAH1-C or the PAH6-C, i.e., only one phage, and also comprise both two phages. Further, it may further comprise an active bacteriophage other than the phage, and the active bacteriophage may preferably be a phage having the bacteriolytic activity to *Aeromonas hydrophila*, but not limited thereto, and it also includes a phage having the bacteriolytic activity to other bacteria.

Further, when treating the composition for inhibiting growth of *Aeromonas hydrophila* or killing thereof, the antibiotic, the antiseptic and the feed additive, general methods, which were used for inhibiting growth of bacteria including *Aeromonas hydrophila* or killing thereof in the past, can be used in combination, and preferably, general methods, which were used for inhibiting growth of *Aeromonas hydrophila* or killing thereof in the past, can be used in combination.

As further another embodiment, the present invention relates to a pharmaceutical composition for preventing or treating *Aeromonas hydrophila* infectious disease comprising the phage or its culture as an active ingredient, or a method for preventing or treating the *Aeromonas hydrophila* infectious disease by using the same.

As described above, the phage according to the present invention having the specific killing activity to *Aeromonas hydrophila* shows an effect on preventing or treating various diseases caused by *Aeromonas hydrophila* infection.

Preferably, the *Aeromonas hydrophila* infectious disease is septicemia, *Aeromonas* disease or an ulcer, but not limited thereto. Further, the *Aeromonas hydrophila* infectious disease includes symptoms expressed from the diseases, for example, diarrhea or bleeding, but not limited thereto.

In the specification of the present invention, the term 'preventing or treating' means preventing, inhibiting or relieving the *Aeromonas hydrophila* infectious disease.

The composition of the present invention can be administered into an animal in the form of a pharmaceutical formulation, or by feeding after mixing thereof into a feed or drinking water.

The composition of the present invention can be administered through a variety of routes such as an oral route or a parenteral route only if the composition can reach a target tissue, and specifically, it can be administered through general methods such as oral, rectal, topical, intravenous, intrapenitoneal, intra-muscular, intra-arterial, transdermal, intranasal, inhalation.

The method of the present invention for preventing or treating includes administrating the composition of the present invention with a pharmaceutically effective dose. It is obvious to a person having ordinary skill in the art that the suitable daily dose can be decided by a doctor in charge within the scope of proper medical judgment. It is preferred that the therapeutically effective dose for a specific subject may be differently determined according to various factors or pseudo-factors well-known in the medical field, for example, the kind and extent of reaction to be achieved, age, body weight, general health conditions, gender and diet of the subject, administration time, administration route, distribution ratio of composition, treatment duration and drug used together or simultaneously with the specific compositions.

The newly isolated phage ASP-1 according to the present invention has an effect on inhibiting growth of *Aeromonas salmonicida* or killing thereof, and particularly, also has an activity of inhibiting growth of antibiotic resistant *Aeromonas salmonicida* or killing thereof. Accordingly, it is effective for preventing or treating *Aeromonas salmonicida* infectious diseases such as furunculosis or septicemia, and can be used as an antibiotic or an antiseptic as well as a feed.

Further, the newly separated phage PVP-1 according to the present invention has an effect on inhibiting growth of *Vibrio parahaemolyticus* or killing thereof, and particularly, also has an activity of inhibiting growth of multi-drug resistant (or antibiotic resistant) *Vibrio parahaemolyticus* or killing thereof. Accordingly, it is effective for preventing or treating *Vibrio parahaemolyticus* infectious diseases such as gastroenteritis, food poisoning or infection of wound, and can be used as a feed, an antibiotic or an antiseptic as well as a composition for treating ballast water.

The newly isolated phage PAH1-C or PAH6-C according to the present invention has an effect on inhibiting growth of *Aeromonas hydrophila* or killing thereof, and particularly, also has an activity of inhibiting growth of antibiotic resistant *Aeromonas hydrophila* or killing thereof. Accordingly, it is effective for preventing or treating *Aeromonas hydrophila* infectious diseases such as septicemia, *aeromonas* disease or an ulcer, and can be used as an antibiotic or an antiseptic as well as a feed.

Thus, using these newly isolated phages is expected to attribute to competitiveness of aquaculture industry and improvement of national health.

Hereinafter, preferred embodiments of the present disclosure will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation. Therefore, the description proposed herein is just a preferable example for the purpose of illustrations only, not intended to limit the scope of the disclosure, so it should be understood that other equivalents and modifications could be made thereto without departing from the spirit and scope of the disclosure.

EXAMPLES

[Example about Novel Phage ASP-1 and its Use for Inhibiting Growth of *Aeromonas salmonicida*]

<Materials and Methods>

Bacteria Strain

In this experiment, 17 *Aeromonas salmonicida* species of 3 different subspecies and 20 species of motile *Aeromonas* genus (10 *A. hydrophila*, 5 *A. sorbia* and 5 *A. media*) and 11 other strains were used (see Table 1). The bacterial strains were cultured in tryptic soy broth (TSB), or all *Aeromonas* strains were sub-cultured on tryptic soy agar at 20° C. and other bacterial strains of different genus were sub-cultured on tryptic soy agar at 37° C. All strains were stored at −80° C. with 10% glycerol until used.

TABLE 1

| Bacterial species (n) | Strain | Host range[a] | EOPs[b] | Source[c] |
|---|---|---|---|---|
| *A. salmonicida* subsp. *salmonicida* (15) | AS01 | ++ | 1.00 | [12] |
| | AS02 | ++ | 0.68 ± 0.06 | [12] |
| | AS04 | ++ | 2.04 ± 0.02 | [12] |
| | AS05 | ++ | 0.2 ± 0.05 | [12] |
| | AS06 | + | 0.87 ± 0.13 | [12] |
| | AS07 | + | 0.08 ± 0.02 | [12] |
| | AS08 | + | 0.08 ± 0.01 | [12] |
| | AS09 | ++ | 3.24 ± 0.26 | [12] |
| | AS10 | + | 0.98 ± 0.10 | [12] |
| | AS11 | ++ | 0.31 ± 0.05 | [12] |
| | AS12 | + | 0.57 ± 0.03 | [12] |
| | AS13 | ++ | 0.16 ± 0.02 | [12] |
| | AS14 | ++ | 0.09 ± 0.02 | [12] |
| | AS15 | ++ | 0.23 ± 0.05 | [12] |
| | ATCC 33658 | ++ | 0.92 ± 0.10 | 3 |
| *A. salmonicida* subsp. *achromogenes* (1) | AS03 | ++ | 0.32 ± 0.06 | [12] |

TABLE 1-continued

| Bacterial species (n) | Strain | Host range[a] | EOPs[b] | Source[c] |
|---|---|---|---|---|
| *A. salmonicida* subsp. *masoucida* (1) | ATCC 27013 | ++ | 1.35 ± 0.13 | 3 |
| *A. hydrophila* (10) | SNUFPC-A3 | − | ND[d] | [7] |
| | SNUFPC-A5 | − | ND | [7] |
| | SNUFPC-A6 | − | ND | [7] |
| | SNUFPC-A7 | − | ND | [7] |
| | SNUFPC-A8 | − | ND | [7] |
| | SNUFPC-A9 | − | ND | [7] |
| | SNUFPC-A10 | − | ND | [7] |
| | SNUFPC-A11 | − | ND | [7] |
| | SNUFPC-AH1 | − | ND | [7] |
| | SNUFPC-AH2 | − | ND | [7] |
| *A. media* (5) | SNUFPC-A17 | − | ND | [7] |
| | SNUFPC-A22 | − | ND | [7] |
| | SNUFPC-A23 | − | ND | [7] |
| | SNUFPC-A24 | − | ND | [7] |
| | SNUFPC-A25 | − | ND | [7] |
| *A. sobria* (5) | SNUFPC-A1 | − | ND | [7] |
| | SNUFPC-A2 | − | ND | [7] |
| | SNUFPC-A4 | − | ND | [7] |
| | SNUFPC-A16 | − | ND | [7] |
| | SNUFPC-A26 | − | ND | [7] |
| *Streptococcus imae* | ATCC 29178 | − | ND | 3 |
| *S. agalactiae* | ATCC 27956 | − | ND | 3 |
| *S. suis* | Ss-1 | − | ND | 1 |
| *Enterococcus faecium* | CCARM 5192 | − | ND | 2 |
| *E. faecalis* | CCARM 5168 | − | ND | 2 |
| *Vibrio vulnificus* | ATCC 27562 | − | ND | 3 |
| *V. parahaemolyticus* | ATCC 17802 | − | ND | 3 |
| *V. algynolyticus* | ATCC 17749 | − | ND | 3 |
| *Staphylococcus aureus* | SA1 | − | ND | 1 |
| *Listeria monocytogenes* | LM01 | − | ND | 1 |
| *Escherichia coli* | DH10B | − | ND | 4 |

[a]++, clear plaque; +, turbid plaque; −, no plaque
[b]The EOP values were shown as mean ± SD
[c]1, laboratory collection; 2, obtained from the Culture Collection of Antimicrobial Resistant Microbes in Korea; 3, purchased from the American Type Culture Collection; 4, purchased from Invitrogen
[d]Not done

[12]: Kim J H, Hwang S Y, Son J S, Han J E, Jun J W, Shin S P, Choresca C H, Choi Y J, Park Y H, Park S C (2011) Molecular characterization of tetracycline- and quinolone-resistant *Aeromonas salmonicida* isolated in Korea. J Vet Sci 12:41-48.

[7]: Han J E, Kim J H, Choresca C H, Shin S P, Jun J W, Chai J Y, Han S Y, Park S C (2011) First description of the qnrS-like (qnrS5) gene and analysis of quinolone resistance-determining regions in motile *Aeromonas* spp. from diseased fish and water. Res Microbiol. doi:10.1016/j.resmic.2011.09.001.

Phage Isolation and Host Range Determination

The conventional double-layered agar method described (AdamsM (1959) Bacteriophages. Interscience Publishers, New York) was used for the phage isolation and enumeration of its plaque-forming units (PFUs). One of the previously confirmed antibiotic-resistant *Aeromonas salmonicida* subsp. *salmonicida* strains, AS01, was used as a host bacterial strain for the phage isolation. Plaque morphologies were observed after 18-24 hrs of incubation. Bacterial cultures in exponential phase were inoculated with sediment samples or water from the rainbow trout culture farms in Korea. The mixtures were incubated for 36 hrs at 20° C., centrifuged for 20 min at 10,000×g, and filtered through a 0.45 µm size filter. Pure phage strain was obtained by three serial single-plaque isolations and designated as ASP-1. The filtered phage lysate was precipitated with 10% (wt/vol) polyethylene glycol 8000 in 1 M NaCl at 4° C. for 12 hrs and collected by centrifugation at 10,000×g for 10 min at 4° C.

The purified phage was prepared by CsCl step gradients ultracentrifugation (density gradient: 1.15, 1.45, 1.50 and 1.70 g/ml; 250,000×g; 22 hrs; 4° C.), dialyzed in SM buffer (10 mM NaCl, 50 mM Tris [pH7.5] and 10 mM $MgSO_4$) and stored at 4° C. until used.

The host range of ASP-1 was determined by dropping 10 μl of diluted phage suspension ($3.3 \times 10^7$ PFU/ml) in double-layered agar plates inoculated with all the 37 Aeromonas subsp. and other bacterial species. Then, all the Aeromonas subsp. strains were incubated at 20° C. and other bacterial strains were incubated at 37° C. for 20 hrs, and checked for the presence or the absence of plaque formation. The plaque-forming ability of the phage against each strain was also measured as the efficiency of plating (EOP). Diluted phage suspension ($3.5 \times 10^4$ PFU/ml) was assayed by the double-layered agar method against each phage-susceptible bacterial strain showing clear plaques, and the number of plaques was determined after 24 hr incubation. The EOP values were quantified by calculating the ratio of PFU obtained with each phage-susceptible strain to PFU obtained with Aeromonas salmonicida subsp. salmonicida AS01.

Electron Microscopy

The purified phage sample was loaded onto a copper grid followed by negative staining with 2% uranyl acetate and drying. The morphology of the phage was observed using a Zeiss TEM EM902 (Zeiss) at voltage of 80 kV. Phage sizes were calculated by the means of at least ten measurements.

One-Step Growth

The 10 μl of purified phage suspension ($9.3 \times 10^9$ PFU/ml) was added to 10 ml of inoculums of the host bacterial strain AS01 in early exponential phase ($OD_{600}$: 0.2) in TSB, and absorbed for 5 min and then centrifuged at 10,000×g for 1 min. After the supernatants were removed, the pellets containing the phages-infected bacterial cells were suspended in 20 ml of fresh TSB and incubated with shaking at 250 rpm at 20° C. Partial samples were taken at 10-min intervals for 120 min, and the titrations from the aliquots were immediately determined.

Phage Genome Analysis

Purified phage genomic DNA (gDNA) was prepared as described in Son J S et al., (2010) Complete genome sequence of a newly isolated lytic bacteriophage, EFAP-1 of Enterococcus faecalis, and antibacterial activity of its endoly sin EFAL-1. J Appl Microbiol 108:1769-1779, and was subjected to nuclease treatment using DNase I (20 U/μl), RNase A (5 U/μl) and Mung bean nuclease (20 U/μl) (Takara) according to the manufacturer's instructions. In addition, the size estimation and restriction analysis of phage gDNA were performed by pulsed-field gel electrophoresis as previously described in Uchiyama J et al., (2008) Isolation and characterization of a novel Enterococcus faecalis bacteriophage EF24C as a therapeutic candidate FEMS Microbiol Lett 278:200-206, with some modifications. Briefly, 500 μl of phage suspension was mixed with 2% (wt/vol) NuSieve GTG agarose (FMC BioProducts), dispensed into plug molds and solidified. The plugs were punched out of the molds into a small volume of digestion buffer (500 mM EDTA, 10 mM Tris [pH 8.0], 1% SDS [wt/vol] and 1 mg/ml of proteinase K) and incubated at 50° C. overnight. The digestion buffer was decanted, and the samples were washed three times using TE buffer and then digested with 10 U of SacII, Sau3AI, MspI, XbaI, NotI, HindIII, SmaI, SphI, NcoI, HpaII, SpeI and EcoRI (New England Biolabs) for 1 hr at 37° C., respectively. The plugs were washed three times using TE buffer, placed in wells of 1.2% Pulsed-Field Certified agarose (Bio-Rad) in 0.5×TBE and overlaid with molten 0.5% NuSieve GTG agarose. The samples were electrophoresed using a CHEF-DR III System (Bio-Rad) at 6 V/cm with pulse ramps from 5 to 15 sec for 16 hrs at 14° C. in 0.5×TBE buffer.

The phage genome sequencing was performed by Macrogen Inc. (Korea). Phage gDNA was sheared using a nebulizer (Invitrogen) and blunt-end repaired. DNA fragments of the desired size (2-3 kb) were blunt-end ligated into the pCR4 blunt-TOPO vector (Invitrogen) and introduced into E. coli DH10B. Partial genome sequences were obtained by sequencing with primer walking. The potential ORFs were predicted using GeneMark.hmm, and gene sequence homology was investigated using the NCBI BlastP program (http://blast.ncbi.nlm.nih.gov/Blast.cgi).

Phage Proteome Analysis

Phage ghosts were prepared as previously described in Konopa G, Taylor K (1979) Coliphage λ ghosts obtained by osmotic shock or LiCl treatment are devoid of J- and H-gene products. J Gen Virol 43:729-733. Purified phage suspension ($8.4 \times 10^{11}$ PFU/ml) was re-concentrated by ultracentrifugation at 100,000×g at 4° C. for 30 min. They were re-suspended in 10 M LiCl, heated to 46° C. for 20 min and then tenfold diluted with 50 mM Tris/HCl (pH 8.0) in 100 mM NaCl and 5 mM $MgCl_2$, and treated with DNase I (20 U/μl) (Takara) for 2 hrs at 37° C. Prepared phage ghosts were then analyzed by standard Tris-glycine sodium dodecyl sulfate polyacrylamide gel electrophoresis (SDS-PAGE) using SDS Ready-Gel (4 to 20% polyacrylamide gradient; Bio-Rad) and stained by PlusOne™ Silver Staining Kit, Protein (GE Healthcare). Protein bands were extracted from the gels, digested with trypsin and identified by liquid chromatography-tandem mass spectrometry (LC-MS/MS) using the proteomics platform at the National Instrumentation Center for Environmental Management (NICEM) at Seoul National University. All MS/MS data were searched using ProteinPilot™ 3.0 Software (Applied Biosystems) against the GenBank non-redundant protein database.

Host Cell Lysis Test

Among the phage-sensitive Aeromonas salmonicida, AS01 (A. salmonicida subsp. salmonicida), AS03 (A. salmonicida subsp. achromogenes) and ATCC 27013 (A. salmonicida subsp. masoucida) were used for evaluation of bacteriolytic activity of ASP-1. The purified phage and three Aeromonas salmonicida strains in early exponential phase ($OD_{600}$: 0.1) were co-cultured in 10 ml of fresh TSB at doses of MOI (multiplicity of infection): 0, 0.1, 1 and 10. The preparations were incubated with shaking at 250 rpm at 20° C. Bacteria inoculated into TSB without phage (MOI: 0) were used as a control. The absorbance ($OD_{600}$) was determined 0, 3, 6, 12 and 24 hrs after inoculation, respectively.

Examination of Effect of ASP-1 Phage Against Test Fish Artificially Infected with Aeromonas Salmonicida A rainbow trout (Oncorhynchus mykiss, 4-5 weeks old, average body length: 15.5 cm, average body weight: 24.71 g), which is known for having the highest sensitivity to Aeromonas salmonicida, was used. As Aeromonas salmonicida used for artificial infection, AS09 strain having TTSS (type III secretion system) gene was used. Infection was conducted by intra-muscular injection, and also the ASP-1 was injected by the same method. 4 test groups were composed in total: a group not treated after bacterial infection (20 fishes), a group treated with phage after bacterial infection (20 fishes), a group injected with only phage (20 fishes) and a group injected with only PBS (20 fishes). The AS09 strain used for bacterial infection was artificially infected after diluted at the concentration of $2.97 \times 10^3$ CFU/fish with PBS, and ASP-1, the phage used for treatment, was inoculated at the concentration of $1.9 \times 10^8$ CFU/fish. Prognosis of each test group was observed in a water bath of water temperature of 18° C. for 14 days.

<Result>

Morphology, Host Range and One-Step Growth of *Aeromonas* Phage ASP-1

One phage, designated as ASP-1, was isolated from the sediment samples of the rainbow trout culture farm and formed approximately 2 mm plaques in *Aeromonas* salmonicida subsp. *salmonicida* AS01 strain. The phage was morphologically classified into the family Myoviridae, the order Caudovirales and morphotype A1 (an icosahedral head and long contractile sheathed tails) (FIG. 1), according to the classification of Ackermann. The tail length and width were 123±18 nm (mean±SD) (n=10) and 16±2 nm (n=10), respectively, and the head diameter was 53±7 nm (n=10).

To evaluate the host range of ASP-1, it was tested on various motile *Aeromonas* genus as well as *Aeromonas*

For the genome analysis of the ASP-1, a preliminary phage genome database was constructed by random shotgun sequencing. We were able to find four partial ORF sequences of phage-related proteins (RNA polymerase, DNA polymerase, large subunit terminase and tail fiber) and three complete ORF sequences (muramidase, head portal protein and hypothetical protein) by BlastP searches in the GenBank database. And the amino acid size, identity and E values are shown in Table 2. The predicted RNA polymerase, DNA polymerase, large subunit terminase and one hypothetical protein of ASP-1 showed similarity to those of enterobacteria phage φpEcoM-GJ1 (GenBank accession number NC_010106), and the predicted tail fiber and putative muramidase proteins were homologous with *Aeromonas* phage φO18P (GenBank accession number NC_009542), which was classified as a P2-like Myoviridae phage.

TABLE 2

| No. | Amino acid size | Amino acid identity (%) | Putative functions [organism] | E-value | GenBank accession No. |
| --- | --- | --- | --- | --- | --- |
| 1 | 80 | — | DNA polymerase [Enterobacteria phage φEcoM-GJ1] | 3e-14 | JF342633 |
| 2 | 135 | — | large subunit terminase [Enterobacteria phage φEcoM-GJ1] | 5e-47 | JF342686 |
| 3 | 338 | — | RNA polymerase [Enterobacteria phage φEcoM-GJ1] | 1e-44 | JF342689 |
| 4 | 136 | — | putative tail fiber protein [*Aeromonas* phage φO18P] | 3e-05 | JF342690 |
| 5* | 153 | 125/153 (82) | putative muramidase [*Aeromonas* phage φO18P] | 6e-72 | JF342687 |
| 6* | 431 | 197/383 (52) | head portal protein [*Xanthomonas* phage phiL7] | 2e-117 | JF342688 |
| 7* | 145 | 42/148 (29) | hypothetical protein [Enterobacteria phage φEcoM-GJ1] | 2e-11 | JF342684 |

*complete ORFs

Figure 2:
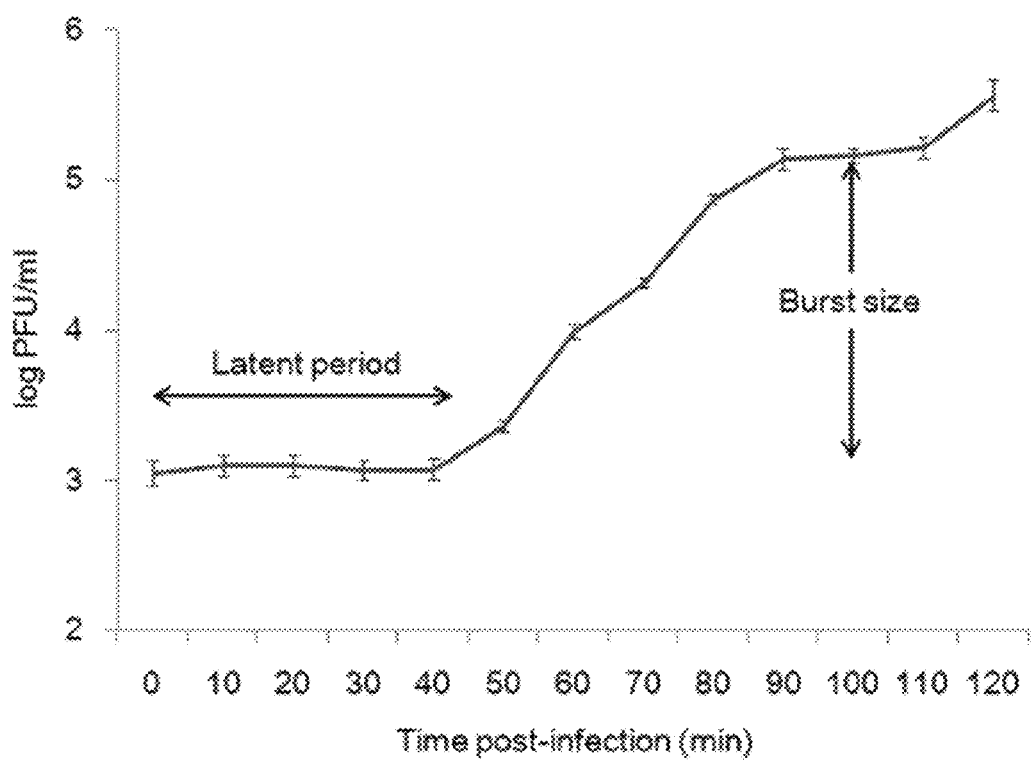
FIG. 2 shows one-step growth of phage ASP-1 in *Aeromonas salmonicida* subsp. *salmonicida* AS01. The results show means±standard deviations, and latent time and burst size were obtained from the triplicate experiments.

*salmonicida* strains. Among the 14 antibiotic-resistant *Aeromonas salmonicida* subsp. *salmonicida*, 9 strains produced completely clear plaques in double-layer agar, whereas the other 5 strains developed turbid plaques. Therefore, all 14 *Aeromonas salmonicida* subsp. *salmonicida* were considered to be susceptible to ASP-1. *Aeromonas salmonicida* subsp. *salmonicida* ATCC 33658, *Aeromonas salmonicida* subsp. *achromogenes* AS03 and *Aeromonas salmonicida* subsp. *masoucida* ATCC 27013 were also considered to have sensitivity (susceptible) to the phage, showing clear plaques. The EOP values varied among the *Aeromonas salmonicida*, and the highest EOP was detected in the multidrug-resistant AS09 strain (Table 1). However, ASP-1 was not able to lyse the other 11 bacterial species or the motile *Aeromonas* genus used in this study. Additionally, one-step growth of ASP-1 was examined to assess the growth pattern and the number of progeny phages released by the lysis of the indicator host strain, AS01. The latent period and the average burst sizes were estimated to be approximately 40 min and 116.7 PFU/cell, respectively (FIG. 2).

Genomic and Proteomic Characteristics of *Aeromonas* Phage ASP-1

Figure 3:
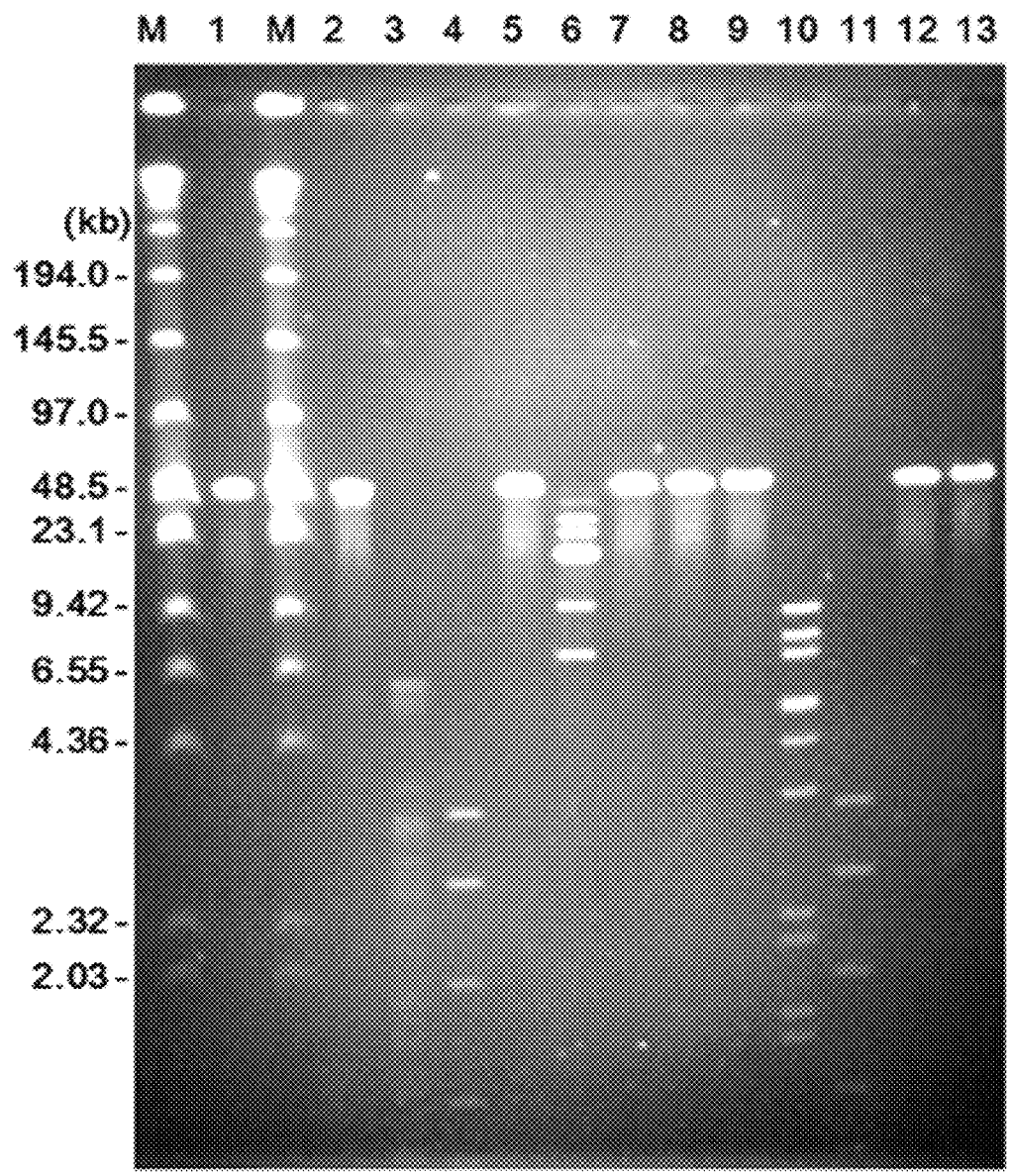
FIG. 3 shows the results of pulsed-field gel electrophoresis of the ASP-1 gDNA and its digestion by 12 restriction endonucleases. Lane M indicates the low-range PFG marker (New England Biolabs). Lane 1 represents the phage gDNA without digestion. Lanes 2 to 13 represent the phage gDNA digestion patterns produced by SacII, Sau3AI, MspI, XbaI, NotI, HindIII, SmaI, SphI, NcoI, HpaII, SpeI and EcoRI (New England Biolabs), respectively. The genome size of ASP-1 was estimated by distinct fragments of NcoI as approximately 48 kb.

In general, Myoviridae phages are known to possess double-strand (ds) DNA genomes. Likewise, the gDNA of ASP-1 was completely digested by DNase I but not by RNase A or Mung bean nuclease; thus, it was presumed to be ds DNA. In addition, the gDNA was digested by Sau3AI, MspI, NotI, NcoI, and HpaII, and its size was estimated by distinct fragments of NcoI as approximately 48 kb (FIG. 3).

Figure 4:
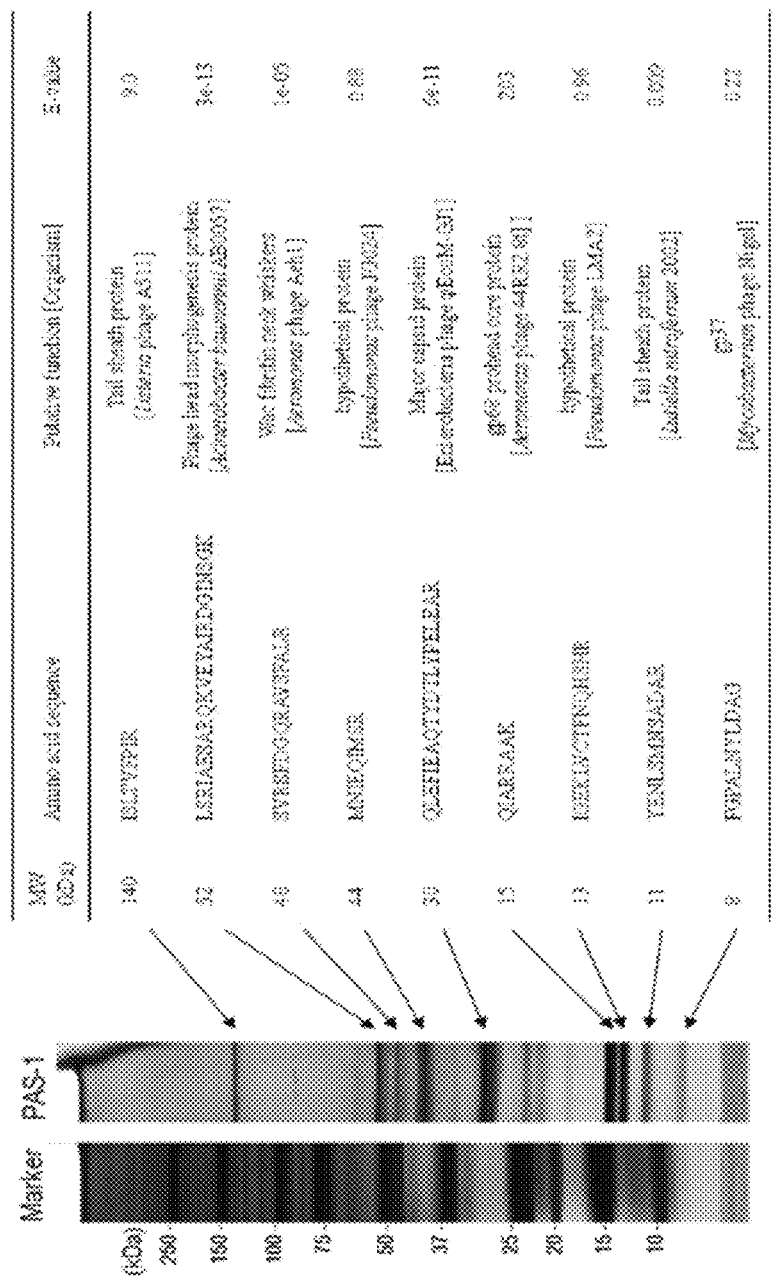
FIG. 4 shows SDS-PAGE profile of ASP-1 virion and their protein profiles by liquid chromatography-mass spectrometry (LC-MS/MS) analysis.

To investigate the structural proteins of ASP-1, purified phage ghosts were subjected to SDS-PAGE and LC-MS/MS analysis. At least 14 distinct protein bands, with molecular masses ranging from 8 to 140 kDa were separated, and 9 major protein bands were subjected to LC-MS/MS for peptide sequencing. From these results, seven partial peptide sequences of structural proteins, comprising tail sheath (140 and 11 kDa), head morphogenesis (52 kDa), wac fibritin neck whiskers (48 kDa), major capsid (30 kDa) and prohead core (15 kDa), were obtained (FIG. 4).

Host Cell Lysis Test of *Aeromonas* Phage ASP-1 Against *Aeromonas salmonicida*

Figure 5A:
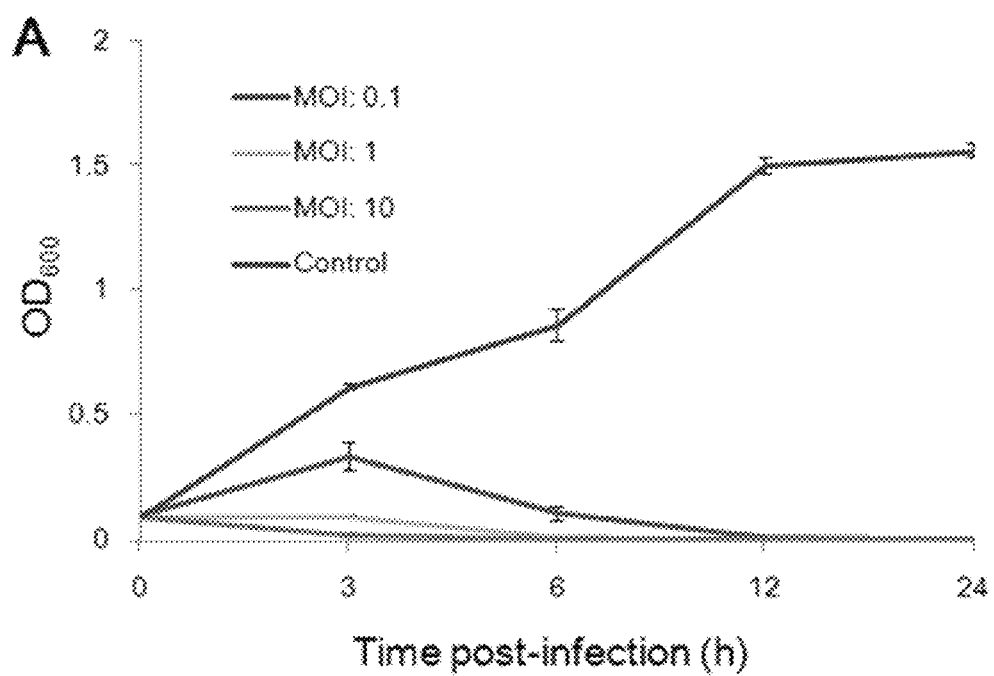
FIG. 5 shows the bacteriolytic activity of ASP-1 against three subspecies of *Aeromonas salmonicida* strains. Pre-exponential cultures of *Aeromonas salmonicida* subsp. *salmonicida* AS01 (FIG. 5A), pre-exponential cultures of *Aeromonas salmonicida* subsp. *achromogenes* AS03 (FIG. 5B) and pre-exponential cultures of *Aeromonas salmonicida* subsp. *masoucida* ATCC 27013 (FIG. 5C) were co-cultured with ASP-1 at MOI of 0, 0.1, 1 and 10, respectively. The results show means±standard deviations from triplicate experiments.
Figure 5B:
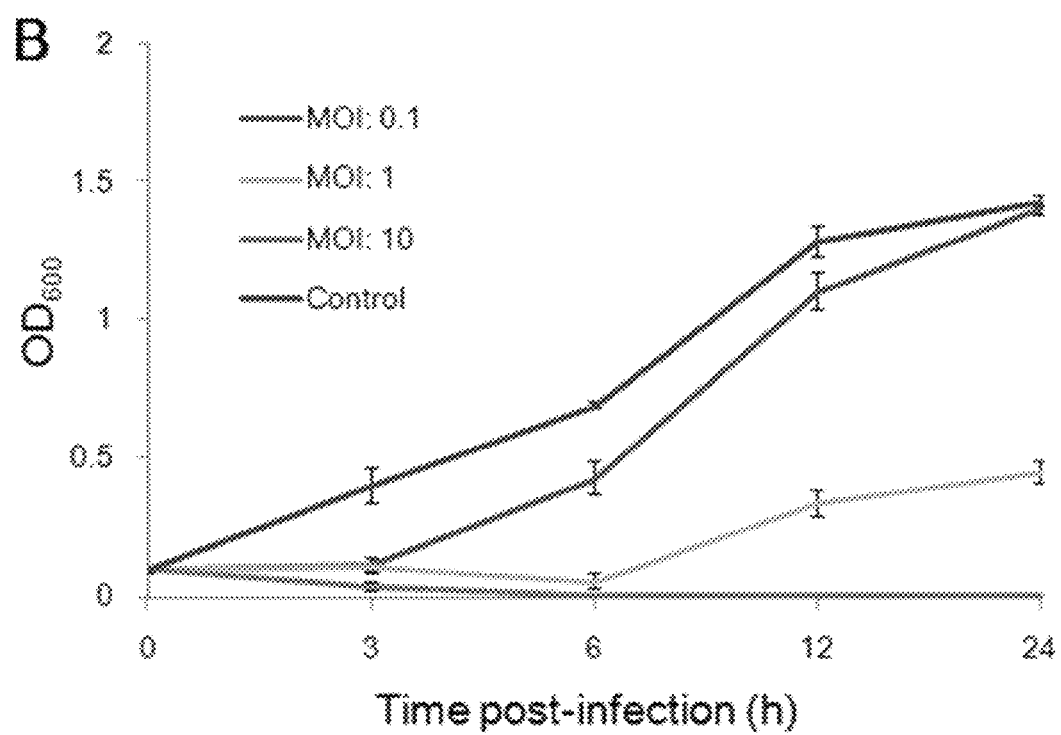
Figure 5C:
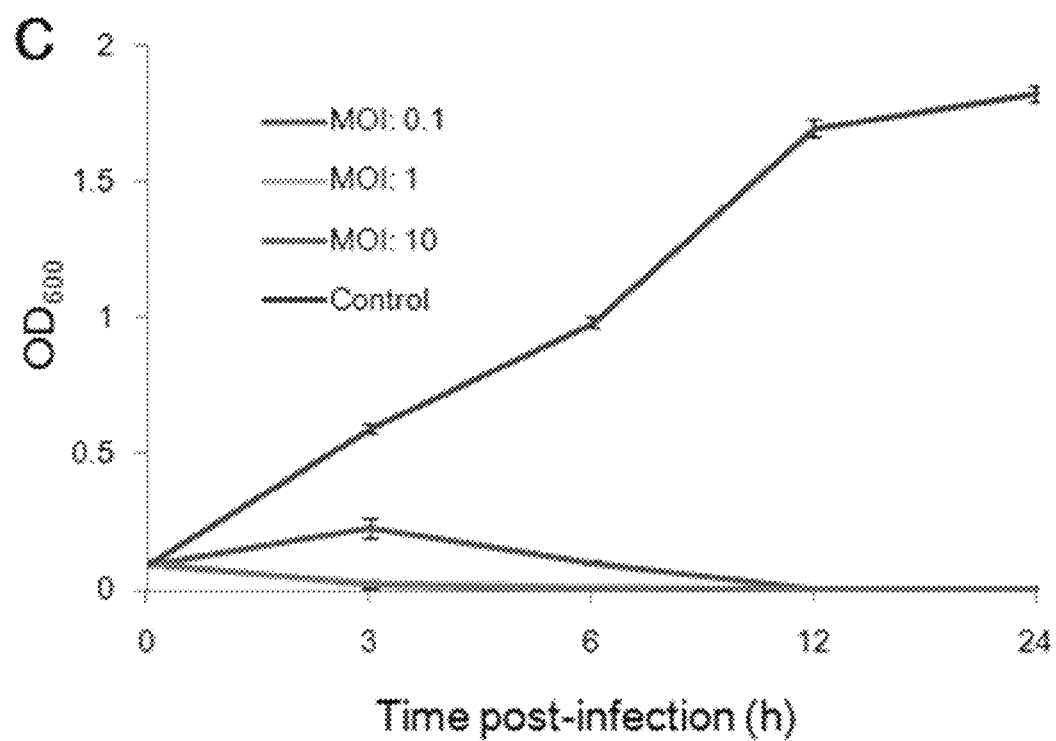

The bacteriolytic activity of ASP-1 was tested on early exponential phase cultures of *Aeromonas salmonicida* subsp. *salmonicida* (AS01), *Aeromonas salmonicida* subsp. *achromogenes* (AS03) and *Aeromonas salmonicida* subsp. *masoucida* (ATCC 27013), respectively (FIG. 5). When the cultures of those three strains were not infected by ASP-1 (MOI: 0), the $OD_{600}$ value continued to increase during the incubations. In contrast, bacterial growths of AS01 and ATCC 27013 strains were apparently retarded at MOI 0.1, 1 and 10 until 24 h after phage ASP-1 infections. However, the bacterial growths of AS03 strain were inhibited only at MOI 10, whereas the $OD_{600}$ values in MOI 0.1 and 1 groups started to increase at 3 and 6 hrs after phage infections and nearly reached 1.5 and 0.5 at 24 hrs, respectively. Additionally, the presences of viable phage-resistant *Aeromonas salmonicida* was determined by plating the lysates of all the phage-inoculated MOI groups (MOI: 0.1, 1 and 10), and phage-resistant colonies were only obtained from the MOI 0.1 and 1 groups of AS03 strain.

Result of Examination of Effect of ASP-1 Phage Against Test Fish Artificially Infected with *Aeromonas Salmonicida*

Figure 6:
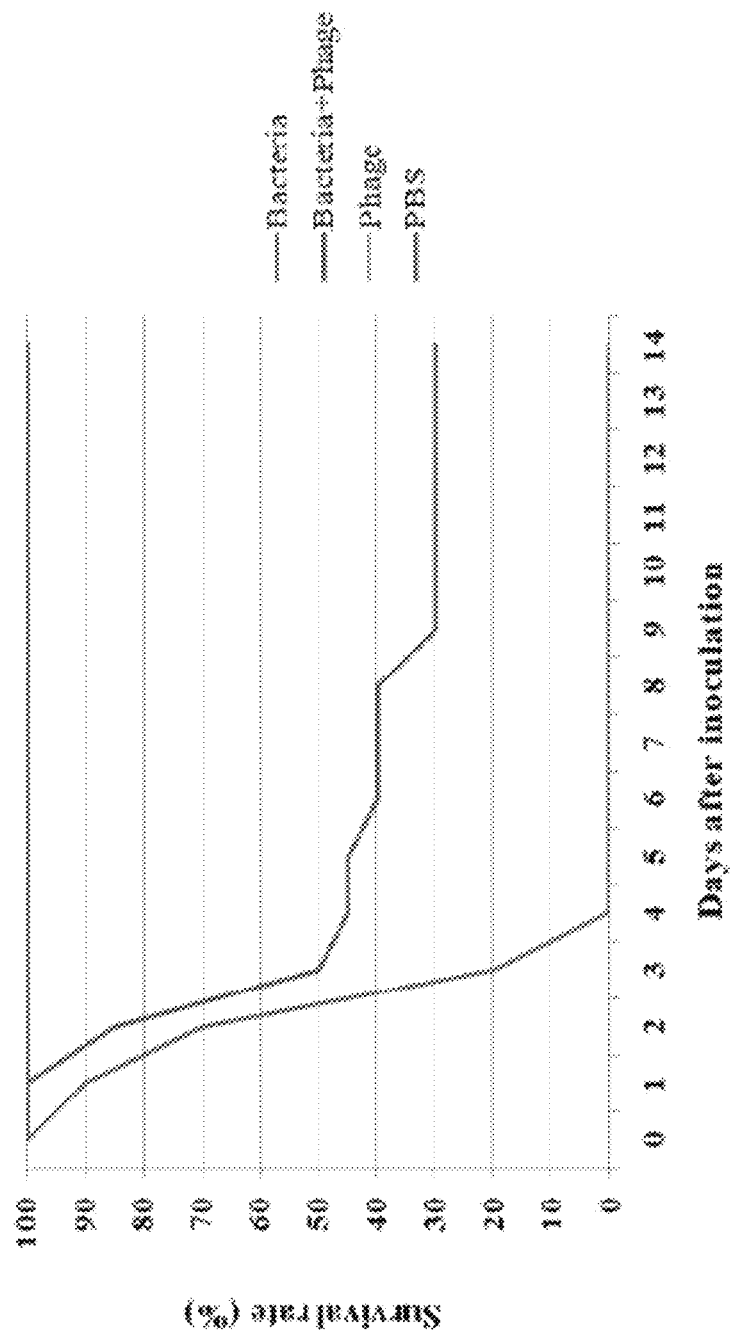
FIG. 6 shows therapeutic effect of the ASP-1 phage against *Aeromonas salmonicida* infection of a rainbow trout.

In the group inoculated with only *Aeromonas salmonicida*, all fishes died within 4 days, and in the group treated with ASP-1, delayed death and reduced death rate were observed. But, in the group inoculated with only phage and the group inoculated only with PBS, death was not observed at all for 14 days (FIG. 6).

Figure 7:
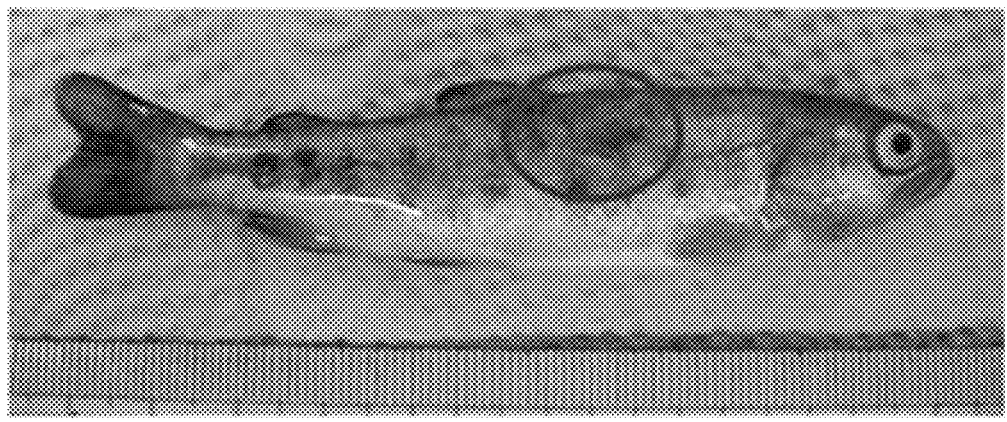
FIG. 7 shows the rainbow trout in the *Aeromonas salmonicida* infected group where furunculosis occurred (a) and the rainbow trout in the ASP-1 treated group where furunculosis did not occur and the infected region was treated (b)
Figure 7:
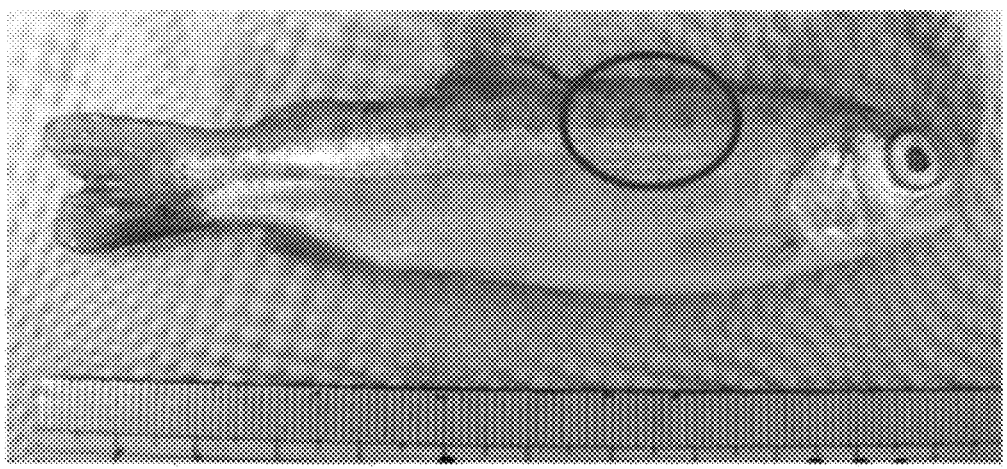

Further, as the result of comparing symptoms between test groups, symptoms of furunculosis were not found in the infected fish treated with ASP-1 (FIG. 7).

Nucleotide Accession Numbers

The nucleotide sequence data of the RNA polymerase, DNA polymerase, large subunit terminase, tail fiber, muramidase, head portal protein and one hypothetical protein gene in the *Aeromonas* phage ASP-1 were deposited in the GenBank database under the accession numbers JF342689, JF342683, JF342686, JF342690, JF342687, JF342688 and JF342684, respectively.

[Example about Novel Bacteriophage PVP-1 and its Use for Inhibiting Growth of *Vibrio parahaemolyticus*]

<Materials and Methods>

Sampling of Subject Bacteria and Phage

At least 100 ml of sediment samples were collected from seawater of oyster farm in the southern sea of Korea and used for phage isolation.

Phage Isolation and Host Range Determination

The conventional double-layered agar method described (AdamsM (1959) Bacteriophages. Interscience Publishers, New York) was used for the phage isolation and enumeration of its plaque-forming units (PFUs). *Vibrio parahaemolyticus* ATCC 33844 was used as a host bacterial strain for the phage isolation. Plaque morphologies were observed after 18-24 hrs of incubation. The isolated materials were incubated for 36 hrs at 20° C., centrifuged for 20 min at 10,000×g, and filtered through a 0.45 µm size filter. 10 ml of 10×TSB was added to 90 ml of the filtered material, and the host bacteria $10^6$~$10^7$ CFU was inoculated thereto followed by incubating at least 12 hrs. Supernatant was collected after centrifugation at 5,000 rpm for 20 min, and the host bacteria $10^8$ was coated on the surface of TSA agar medium and, after dropping 5~10 ul of the supernatant, incubated at 25° C. for 18 hrs. After diluting the lyzed bacteria 10-times, titer was measured and plaque shape was observed. Pure phage strain was obtained by three serial single-plaque isolations and designated as PVP-1. The filtered phage lysate was precipitated with 10% (wt/vol) polyethylene glycol 8000 in 1 M NaCl at 4° C. for 12 hrs and collected by centrifugation at 10,000×g for 10 min at 4° C. The purified phage was prepared by CsCl step gradients ultracentrifugation (density gradient: 1.15, 1.45, 1.50 and 1.70 g/ml; 250,000×g; 22 hrs; 4° C.), dialyzed in SM buffer (10 mM NaCl, 50 mM Tris [pH7.5] and 10 mM $MgSO_4$) and stored at 4° C. until used.

The host range of PVP-1 was determined by dropping 10 µl of diluted phage suspension ($3.3\times10^7$ PFU/ml) in double-layered agar plates inoculated with *Vibrio parahaemolyticus* and *Vibrio vulnificus*. Then, the bacteria were incubated at 37° C. for 20 hrs, and checked for the presence or the absence of plaque formation.

Genomic Analysis of Isolated phage

Purified phage genomic DNA (gDNA) was prepared as described in Son J S et al., (2010) Complete genome sequence of a newly isolated lytic bacteriophage, EFAP-1 of *Enterococcus faecalis*, and antibacterial activity of its endoly sin EFAL-1. J Appl Microbiol 108:1769-1779, and the presence or the absence of reactivity of the phage genome against DNase I (20 U/µl), RNase A (5 U/µl) and Mung bean nuclease (20 U/µl) (Takara) was examined according to the manufacturer's instructions for phage genomic analysis in advance. First of all, against at least $10^9$ PFU/ml of phage stock, capsid was removed with Proteinase K, supernatant treated with PCI (phenol-chloform-isoamyl alcohol) was treated with isopropanol followed by washing with 70% ethanol, and then genome was finally concentrated in TE buffer. This concentrated phage genome was electrophoresed in 0.7% agarose gel (1×TAE buffer) and used as a control, and each phage group was treated with DNase I and RNase A, Mung bean nuclease followed by judging the result through the presence or the absence of a positive band.

In addition, in order to exactly observe genome size and restriction enzyme cleavage pattern of phage gDNA, pulsed-field gel electrophoresis was conducted as previously described in Uchiyama J et al., (2008) Iso-lation and characterization of a novel *Enterococcus faecalis* bacteriophage EF24C as a therapeutic candidate. FEMS Microbiol Lett 278:200-206, with some modifications. Briefly, 500 µl of phage suspension was mixed with 2% (wt/vol) NuSieve GTG agarose (FMC BioProducts), dispensed into plug molds and solidified. The plugs were punched out of the molds into a small volume of digestion buffer (500 mM EDTA, 10 mM Tris [pH 8.0], 1% SDS [wt/vol] and 1 mg/ml of proteinase K) and incubated at 50° C. overnight. The digestion buffer was decanted, and the samples were washed three times using TE buffer and then digested with 10 U of SacII, Sau3AI, MspI, XbaI, NotI, HindIII, SmaI, SphI, NcoI, HpaII, SpeI and EcoRI (New England Biolabs) for 1 hr at 37° C., respectively. The plugs were washed three times using TE buffer, placed in wells of 1.2% Pulsed-Field Certified agarose (Bio-Rad) in 0.5×TBE and overlaid with molten 0.5% NuSieve GTG agarose. The samples were electrophoresed using a CHEF-DR III System (Bio-Rad) at 6 V/cm with pulse ramps from 5 to 15 sec for 16 hrs at 14° C. in 0.5× TBE buffer.

Electron Microscopy of Isolated Phage

For morphological classification of the isolated phage, observation was conducted by using a transmission electron microscope (TEM). The phage stock was loaded onto a copper grid followed by negative staining with 1% uranyl acetate and drying. Electron microscope imaging was conducted at NICEM of college of agriculture and life science of gwanak campus of Seoul National University. The morphology of the phage was observed using a Zeiss TEM EM902 (Zeiss) at voltage of 80 kV. Phage sizes were calculated by the means of at least ten measurements.

Genomic Analysis of Isolated Phage

Genomic DNA was extracted according to the method known in Sambrook J, Fritsch E F, Maniatis T. 1989. Molecular cloning: a laboratory manual, 2nd ed. Cold Spring Harbor Laboratory Press, Cold Spring Harbor, N.Y., and sequenced by using standard shotgun sequencing reagent and 454 GSFLX Titanium Sequencing System (Roche) (about 50× coverage). Entire genomic sequence was obtained by sequence assembly using SeqMan II sequence analysis software (DNAStar). Putative ORFs (open reading frame) was estimated by using Glimmer 3.02 and GeneMark.hmm, and putative ORF functions were analyzed by using BLASTP and InterProScan. Putative tRNA gene was found by using tRNAscan-SE (v. 1.21) software.

Phage Sensitivity Test Against Host Bacteria in Broth-Culture State

Among many phages in candidate group, phages having excellent underwater viability were selected and used for evaluation of bacteriolytic activity of PVP-1 against *Vibrio*

*parahaemolyticus*. PVP-1 (1.1×10$^9$ PFU/ml) and *Vibrio parahaemolyticus* ATCC 33844 (9.0×10$^6$ CFU/ml) strain was used, and the purified phage and *Vibrio parahaemolyticus* ATCC 33844 were divided into 3 groups of MOI (multiplicity of infection, quantitative ratio of bacteria and bacteriophage): 0.01, 1 and 100 in 10 ml of fresh TSB for experiment. The preparations were incubated with shaking at 250 rpm and 20° C. Bacteria inoculated into TSB without phage (control) were used as a control. The absorbance (OD$_{600}$) was determined up to 24 hrs after inoculation.

<Result>

Phage Isolation and Host Range

One kind of phage was isolated after 11 attempts for isolation in total. The phage was purely isolated through three clonings. The phage designated as PVP-1 was isolated from seawater of oyster farm in the southern sea, and formed plaque on *Vibrio parahaemolyticus* ATCC 33844.

Sensitivity and Host range against the isolated 30 strains of *Vibrio parahaemolyticus* and one kind of *Vibrio vulnificus* was examined, respectively, and determined finally. All of the isolated 30 strains of *Vibrio parahaemolyticus* were multi-drug resistant strains. Among the 30 strains of *Vibrio parahaemolyticus*, 27 strains of *Vibrio parahaemolyticus* formed plaques. Therefore, it was judged that the PVP-1 showed sensitivity to *Vibrio parahaemolyticus*. However, the PVP-1 did not show sensitivity to one kind of *Vibrio vulnificus* used in this study (Table 3).

Figure 8:
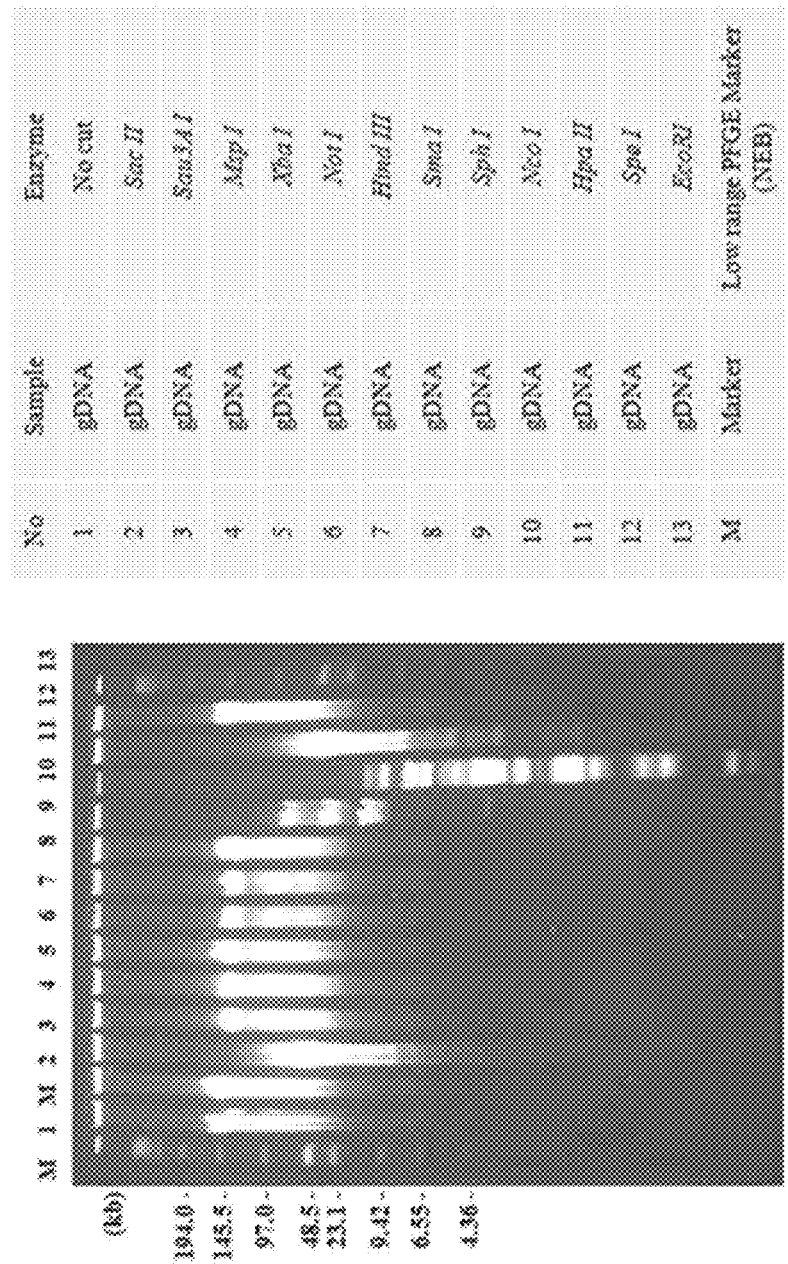
FIG. 8 shows the results of pulsed-field gel electrophoresis of the PVP-1 gDNA and its digestion by 12 restriction endonucleases. Lane M indicates the low-range PFG marker (New England Biolabs). Lane 1 represents the phage gDNA without digestion. Lanes 2 to 13 represent the phage gDNA digestion patterns produced by SacII, Sau3AI, MspI, XbaI, NotI, HindIII, SmaI, SphI, NcoI, HpaII, SpeI and EcoRI (New England Biolabs), respectively. The genome size of PVP-1 was estimated as approximately 100 kb.

RNase A or Mung bean nuclease; thus, it was presumed to be ds DNA. In addition, the gDNA was digested by SphI, NcoI and EcoRI, and its size was estimated as approximately 100 kb (FIG. 8).

2) Morphological Classification of Isolated Phage

Figure 9:
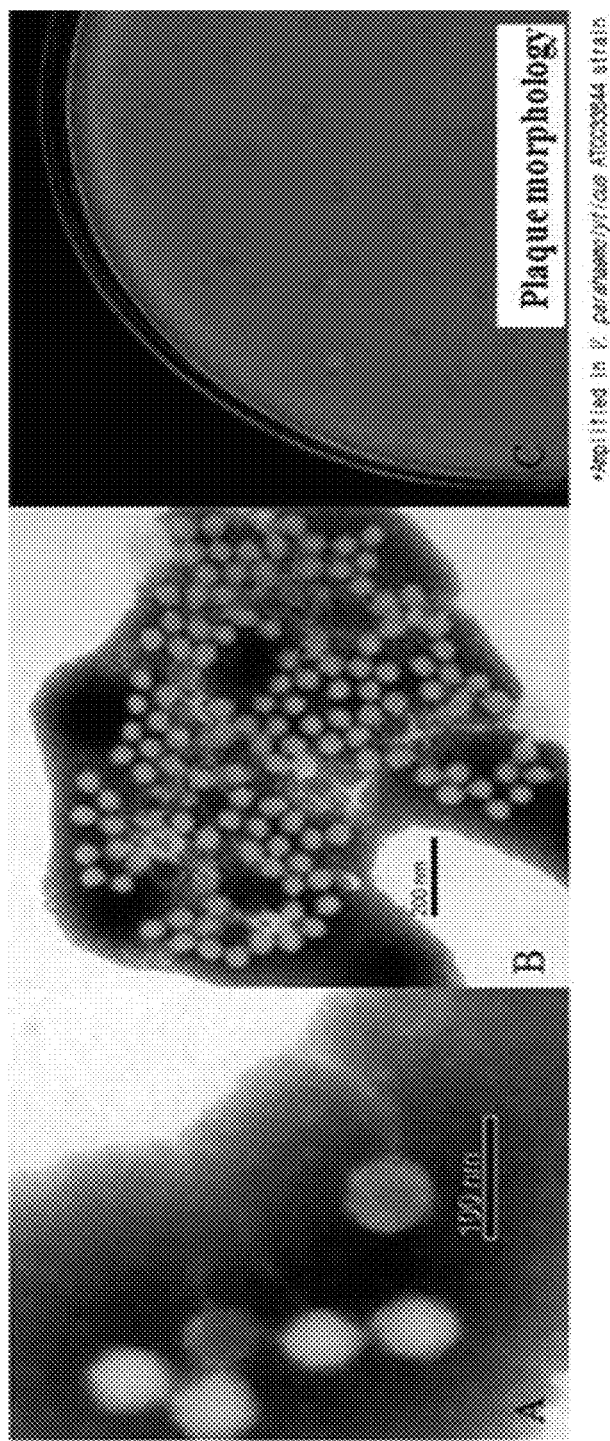
FIG. 9 is the result of observing the negatively stained PVP-1 using an electron microscope. A is an enlarged image of a PVP-1 only, B is an image of a PVP-1 group and C is an image showing that the PVP-1 inhibited growth of *Vibrio parahaemolyticus*, respectively.

The phage was morphologically classified into the family Siphoviridae and the order Caudovirales (FIG. 9), according to the classification of Ackermann. The tail length and width were 129±7 nm (mean±SD) (n=10) and 14±2 nm (n=10), and the head diameter was 63±6 nm (n=10).

Result of Genomic Analysis of PVP-1

The double-stranded and nonredundant DNA genome of PVP-1 was 111,506 bp in length with a G+C content of 39.71%. A total of 157 ORFs containing more than 40 amino acid residues and 19 tRNAs (including 1 pseudogene) were identified, suggesting the PVP-1 as the first bacteriophage in the family Siphoviridae with infectivity to *Vibrio parahaemolyticus*. 45 ORFs showed no homology to proteins in the GenBank database, while 69 and 40 of the other ORFs code for proteins with some homology to known phage- and bacterium-related proteins, respectively. Of the 40 bacterium-related genes in phage PVP-1, 5 ORFs (orf34, orf38, orf79, orf85, and orf97) were highly homologous to *Vibrio*-related proteins and 35 ORFs shared some similarities with unrelated bacteria spanning a wide range of phyla. Bioinformatic analyses were performed for the assignment of putative functions to 69 phage-related ORFs, and those

TABLE 3

| Strain Name | Serial Number | Isolation Place | PVP-1 Sensitivity |
| --- | --- | --- | --- |
| *V. parahaemolyticus* | ATCC27969 | ATCC | + |
| *V. parahaemolyticus* | ATCC33844 | ATCC | ++ |
| *V. parahaemolyticus* | ATCC17802 | ATCC | ++ |
| *V. parahaemolyticus* | VP01 | Corb shell (*Cyclina sinensis*) | + |
| *V. parahaemolyticus* | VP02 | Short neck clam (*Venerupis philippinarum*) | + |
| *V. parahaemolyticus* | VP03 | Sea Mussel (*Mytilus coruscus*) | ++ |
| *V. parahaemolyticus* | VP04 | Sea Mussel (*Mytilus coruscus*) | + |
| *V. parahaemolyticus* | VP05 | Short neck clam (*Venerupis philippinarum*) | ++ |
| *V. parahaemolyticus* | VP06 | Corb shell (*Cyclina sinensis*) | ++ |
| *V. parahaemolyticus* | VP07 | Sea Water | ++ |
| *V. parahaemolyticus* | VP08 | Sea Water | ++ |
| *V. parahaemolyticus* | VP09 | Sea Water | ++ |
| *V. parahaemolyticus* | VP10 | Pacific oyster (*Crassoatrea gigas*) | + |
| *V. parahaemolyticus* | VP11 | Pacific oyster (*Crassoatrea gigas*) | + |
| *V. parahaemolyticus* | VP12 | Pacific oyster (*Crassoatrea gigas*) | − |
| *V. parahaemolyticus* | VP13 | Pacific oyster (*Crassoatrea gigas*) | + |
| *V. parahaemolyticus* | VP14 | Charm abalone (*Hallotis discus hannai*) | ++ |
| *V. parahaemolyticus* | VP15 | Sea Water | − |
| *V. parahaemolyticus* | VP16 | Sea Water | − |
| *V. parahaemolyticus* | VP17 | Sea Water | + |
| *V. parahaemolyticus* | VP18 | Pacific oyster (*Crassoatrea gigas*) | + |
| *V. parahaemolyticus* | VP19 | Sewage | ++ |
| *V. parahaemolyticus* | VP20 | Sewage | + |
| *V. parahaemolyticus* | VP21 | Sewage | + |
| *V. parahaemolyticus* | VP22 | Sea Water | ++ |
| *V. parahaemolyticus* | VP23 | Sea Water | ++ |
| *V. parahaemolyticus* | VP24 | Sea Water | ++ |
| *V. parahaemolyticus* | VP25 | Sea Water | + |
| *V. parahaemolyticus* | VP26 | Sea Water | + |
| *V. parahaemolyticus* | VP27 | Sewage | + |
| *V. vuiniticus* | ATCC33148 | ATCC | − |

\* This test results are sensitivity results of PVP-1 phage to each of *V. parahaemolyticus* and *V. vulniticus* strains after cloning.
The sensitivity was classified into +, ++ depanding on its degree, and − represents strains, which do not show sensitivity at all.

The isolated phages were stored at a dark place of 4° C.

Classification and Characteristics of PVP-1

1) Phage Classification According to Genomic Characteristics

In general, Siphoviridae phages are known to possess double-strand (ds) DNA genomes. Likewise, the gDNA of PVP-1 was completely digested by DNase I but not by ORFs were clustered together by at least three functional roles, i.e., DNA metabolism (orf2, orf3, orf4, orf6, orf7, orf12, orf14, orf15, orf16, orf17, orf18, orf21, orf28, orf32, orf42, and orf52), viral morphogenesis (orf139, orf141, orf143, orf144, orf148, orf149, orf153, orf155, orf156, and orf157), and lytic properties (orf73, orf82, and orf83). Interestingly, most of the ORFs containing DNA metabolism and viral morphogenesis genes were clustered together at each end of the sequenced genome by functional roles and were similar (≤79%) to those of T5 or T5-like phages, thus indicating a close genetic relatedness between pVp-1 and those phages. Thus, it indicates a close genetic relatedness between PVP-1 and those phages. In contrast, there were no sequence similarities to marine *Vibrio* phages belonging to the family Siphoviridae (phiHSIC and SIO-2), and a large proportion of the genes in PVP-1 were not similar to those of other sequenced phages or bacteria, thus it could be considered novel.

The genome sequence of *Vibrio* phage PVP-1 was deposited in the GenBank database under accession number JQ340389.

Figure 10:
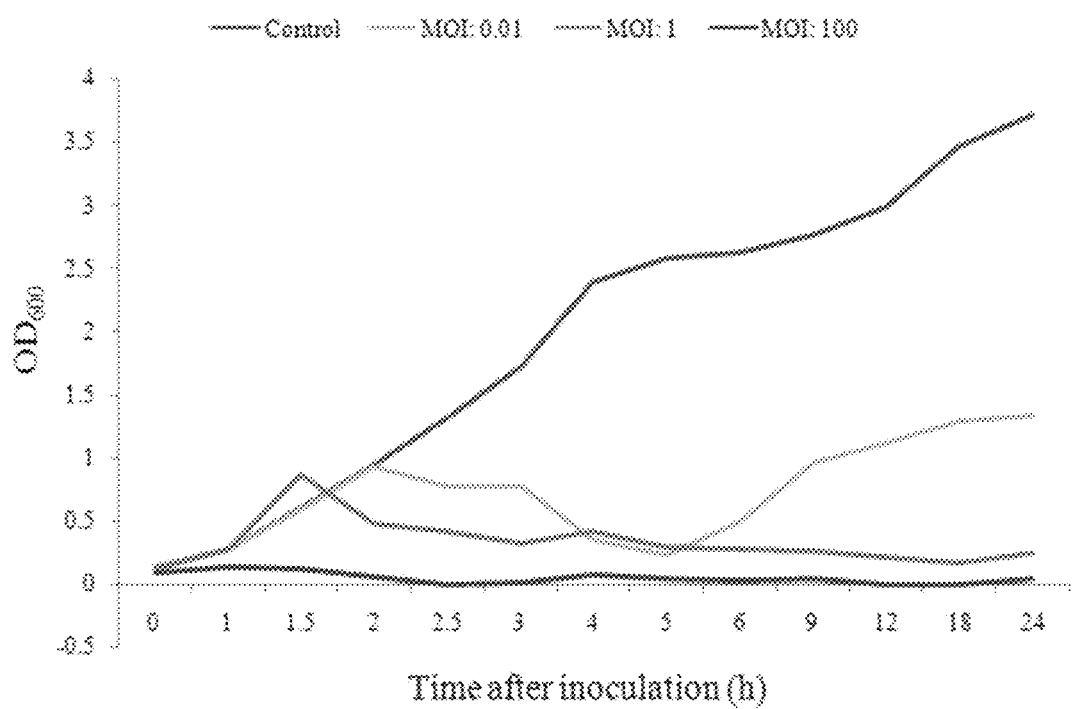
FIG. 10 shows the bacteriolytic activity of the PVP-1 against *Vibrio parahaemolyticus* ATCC 33844, which were co-cultured with the PVP-1 at MOI (multiplicity of infection) of 0.01, 1 and 100, respectively. The results show means±standard deviations from triplicate experiments.

Examination of Effect of PVP-1 Against *Vibrio parahaemolyticus*: Host Cell Lysis Test The bacteriolytic activity of PVP-1 was tested on culture of *Vibrio parahaemolyticus* ATCC 33844 (FIG. 10). When the culture of *Vibrio parahaemolyticus* were not infected by PVP-1 (control), the $OD_{600}$ value continued to increase during the incubations. In contrast, viability of *Vibrio parahaemolyticus* ATCC 33844 was apparently retarded at MOI 0.01, 1 and 100 until 24 h after phage PVP-1 infections.

[Example about Novel Bacteriophage PAH1-C or PAH6-C and its Use for Inhibiting Growth of *Aeromonas hydrophila*]

<Materials and Methods>

Sampling of Subject Bacteria and Phage

Sampling was conducted at sewage treatment plants, rivers, streams around fish culture farms and the like. After marking sampling place and date, at least 500 ml of samples were collected, and each 100 ml out of them were used for bacteriophage isolation. Specifically, bacteriophage was isolated from Seoam stream, Haseong and Nanji water replacement center. Further, bacteria were isolated from aquaculture farms or streams at the same time. The isolated bacteria were identified by using PCR and Vitek II.

Phage Isolation and Host Range Determination

The conventional double-layered agar method described (AdamsM (1959) Bacteriophages. Interscience Publishers, New York) was used for the phage isolation and enumeration of its plaque-forming units (PFUs). *Aeromonas hydrophila* JUNAH was used as a host bacteria for the phage isolation. Plaque morphologies were observed after 18-24 hrs of incubation. The isolated materials were incubated for 36 hrs at 20° C., centrifuged for 20 min at 10,000×g, and filtered through a 0.45 µm size filter. 10 ml of 10×TSB was added to 90 ml of the filtered material, and the host bacteria $10^6$~$10^7$ CFU was inoculated thereto followed by incubating at least 12 hrs. Supernatant was collected after centrifugation at 5,000 rpm for 20 min, and the host bacteria $10^8$ was coated on the surface of TSA agar medium and, after dropping 5~10 ul of the supernatant, incubated at 25° C. for 18 hrs. After diluting the lyzed bacteria 10-times, titer was measured and plaque shape was observed. Pure phage strains were obtained by three serial single-plaque isolations and designated as PAH1-C and PAH6-C. The filtered phage lysates were precipitated with 10% (wt/vol) polyethylene glycol 8000 in 1 M NaCl at 4° C. for 12 hrs and collected by centrifugation at 10,000×g for 10 min at 4° C. The purified phages were prepared by CsCl step gradients ultracentrifugation (density gradient: 1.15, 1.45, 1.50 and 1.70 g/ml; 250,000×g; 22 hrs; 4° C.), dialyzed in SM buffer (10 mM NaCl, 50 mM Tris [pH7.5] and 10 mM $MgSO_4$) and stored at 4° C. until used.

The host ranges of PAH1-C and PAH6-C were determined by dropping 10 µl of diluted phage suspension ($3.3 \times 10^7$ PFU/ml) in double-layered agar plates inoculated with *Aeromonas hydrophila* and *Aeromonas Sorbia*. Then, the bacteria were incubated at 37° C. for 20 hrs, and checked for the presence or the absence of plaque formation.

Genomic Analysis of Isolated Phage

Purified phage genomic DNA (gDNA) was prepared as described in Son J S et al., (2010) Complete genome sequence of a newly isolated lytic bacteriophage, EFAP-1 of *Enterococcus faecalis*, and antibacterial activity of its endoly sin EFAL-1. J Appl Microbiol 108:1769-1779, and the presence or the absence of reactivity of the phage genome against DNase I (20 U/µl), RNase A (5 U/µl) and Mung bean nuclease (20 U/µl) (Takara) was examined according to the manufacturer's instructions for phage genomic analysis in advance. First of all, against at least $10^9$ PFU/ml of phage stock, capsid was removed with Proteinase K, supernatant treated with PCI (phenol-chloform-isoamyl alcohol) was treated with isopropanol followed by washing with 70% ethanol, and then genome was finally concentrated in TE buffer. This concentrated phage genome was electrophoresed in 0.7% agarose gel (1×TAE buffer) and used as a control, and each phage group was treated with DNase I and RNase A, Mung bean nuclease followed by judging the result through the presence or the absence of a positive band.

In addition, in order to exactly observe genome size and restriction enzyme cleavage pattern of phage gDNA, pulsed-field gel electrophoresis was conducted as previously described in Uchiyama J et al., (2008) Iso-lation and characterization of a novel *Enterococcus faecalis* bacteriophage EF24C as a therapeutic candidate. FEMS Microbiol Lett 278:200-206, with some modifications. Briefly, 500 µl of phage suspension was mixed with 2% (wt/vol) NuSieve GTG agarose (FMC BioProducts), dispensed into plug molds and solidified. The plugs were punched out of the molds into a small volume of digestion buffer (500 mM EDTA, 10 mM Tris [pH 8.0], 1% SDS [wt/vol] and 1 mg/ml of proteinase K) and incubated at 50° C. overnight. The digestion buffer was decanted, and the samples were washed three times using TE buffer and then digested with 10 U of SacII, Sau3AI, MspI, XbaI, NotI, HindIII, SmaI, SphI, NcoI, HpaII, SpeI and EcoRI (New England Biolabs) for 1 hr at 37° C., respectively. The plugs were washed three times using TE buffer, placed in wells of 1.2% Pulsed-Field Certified agarose (Bio-Rad) in 0.5×TBE and overlaid with molten 0.5% NuSieve GTG agarose. The samples were electrophoresed using a CHEF-DR III System (Bio-Rad) at 6 V/cm with pulse ramps from 5 to 15 sec for 16 hrs at 14° C. in 0.5×TBE buffer.

Electron Microscopy of Isolated Phage

For morphological classification of the isolated phage, observation was conducted by using a transmission electron microscope (TEM). The phage stock was loaded onto a copper grid followed by negative staining with 1% uranyl acetate and drying. Electron microscope imaging was conducted at NICEM of college of agriculture and life science of gwanak campus of Seoul National University. The morphology of the phage was observed using a Zeiss TEM EM902 (Zeiss) at voltage of 80 kV. Phage sizes were calculated by the means of at least ten measurements.

Phage Sensitivity Test Against Host Bacteria in Broth-Culture State

Bacteriolytic activities of PAH1-C and PAH6-C against *Aeromonas hydrophila* were evaluated. The evaluations were performed by using PAH1-C ($1.1 \times 10^{10}$ PFU/ml) and PAH6-C ($1.1 \times 10^{10}$ PFU/ml), and *Aeromonas hydrophila* AH16 ($8.8 \times 10^6$ CFU/ml) strain, the purified phages and *Aeromonas hydrophila* AH16 were divided into 3 groups of MOI (multiplicity of infection, quantitative ratio of bacteria and bacteriophage): 0.01, 1 and 100 in 10 ml of fresh TSB for experiment. The preparations were incubated with shaking at 250 rpm at 20° C. Bacteria inoculated into TSB without phage (control) were used as a control. The absorbance ($OD_{600}$) was determined up to 24 hrs after inoculation.

Examination of Effect of Phage Against Test Fish Artificially Infected with *Aeromonas hydrophila*

A loach (Cobitis biwae, average body length: 14.56 cm, average body weight: 14.98 g), which is known for having the highest sensitivity to *Aeromonas hydrophila*, was used. As *Aeromonas hydrophila* used for artificial infection, *Aeromonas hydrophila* AH16 strain, which caused mass mortality in the loach, was used, and as phage, PAH1-C and PAH6-C were used. Infection was conducted by intra-muscular injection (IM), and also the phage for treatment was injected by the same method. 4 test groups were composed in total: a group not treated after bacterial infection (20 fishes), a group treated with PAH1-C phage after bacterial infection (20 fishes), a group treated with PAH6-C phage after bacterial infection (20 fishes) and a group treated with PAH1-C phage and PAH6-C phage at the same time after bacterial infection (20 fishes). Further, each experiment was repeated three times to obtain more accurate results. The AH16 strain used for bacterial infection was artificially infected after being diluted at the concentration of $3.3 \times 10^7$ CFU/fish with PBS, the PAH1-C and the PAH6-C, used for treatment, were inoculated at the concentrations of $1.1 \times 10^9$ CFU/fish and $1.0 \times 10^9$ PFU/fish, respectively. Prognosis of each test group was observed in a water bath of water temperature of 25° C. for 7 days.

<Result>

Phage Isolation and Host Range

Two kinds of phages were isolated after 11 attempts for isolation in total. The phages were purely isolated through three clonings. The phage designated as PAH1-C was isolated from Seoam stream, Haseong and formed plaque on *Aeromonas hydrophila* JUNAH. Further, the phage designated as PAH6-C was isolated from Nanji water replacement center and formed plaque on *Aeromonas hydrophila* JUNAH.

Sensitivity and Host range against each of the two kinds of phages by using the isolated total 8 strains of *Aeromonas hydrophila* and 10 strains of *Aeromonas Sorbia* as a subject was examined, respectively, and determined finally. PAH1-C formed plaques on 6 strains of *Aeromonas hydrophila* out of 7 strains of *Aeromonas hydrophila* and 1 strain of *Aeromonas Sorbia* out of 10 strains of *Aeromonas Sorbia*. Moreover, PAH6-C formed plaques 4 strains of *Aeromonas hydrophila* out of 7 strains of *Aeromonas hydrophila* and 1 strain of *Aeromonas Sorbia* out of 10 strains of *Aeromonas Sorbia*.

Therefore, it was judged that both of the PAH1-C and PAH6-C showed sensitivity to *Aeromonas hydrophila* (Table 4). All *Aeromonas hydrophila* of the following Table 4 are antibiotic resistant strains, and particularly, *Aeromonas hydrophila* JUNAH of *Aeromonas hydrophila* used as host bacteria is a multi-drug resistant strain.

TABLE 4

| Strain Name | Serial Num. | Isolation Place | Sensitivity PAH1-C | PAH6-C |
|---|---|---|---|---|
| *A. hydrophila* | AH1 | Koi (*Cyprinus carpio carpio*) | + | − |
| *A. hydrophila* | AH6 | Congo tetra (*Phenacogrammus interruptus*) | + | − |
| *A. hydrophila* | AH7 | Sailifin molly (*Poecilia latipinna*) | − | + |
| *A. hydrophila* | AH9 | Cherry salmon (*Oncorhynchus masou masou*) | + | − |
| *A. hydrophila* | AH16 | Loach (*Cobitis biwae*) | ++ | + |
| *A. hydrophila* | AK1 | Han Liver | + | ++ |
| *A. hydrophila* | AK9 | Sewage in Gyeonggi province | ++ | ++ |
| *A. Sorbia* | AS1 | Goldfish (*Carassius auratus auratus*) | + | + |
| *A. Sorbia* | AS2 | Neon tetra (*Paracheirodon innesi*) | − | − |
| *A. Sorbia* | AS3 | Koi (*Cyprinus carpio carpio*) | − | − |
| *A. Sorbia* | AK2 | Lake | − | − |
| *A. Sorbia* | AK3 | Lake | − | − |
| *A. Sorbia* | AK4 | Lake | − | − |
| *A. Sorbia* | AK5 | Lake | − | − |
| *A. Sorbia* | AK6 | Lake | − | − |
| *A. Sorbia* | AK7 | Lake | − | − |
| *A. Sorbia* | AK8 | Lake | − | − |

The isolated phages were stored at a dark place of 4° C.

Classification and Characteristics of PAH1-C and PAH6-C

1) Phage Classification According to Genomic Characteristics

Figure 11:
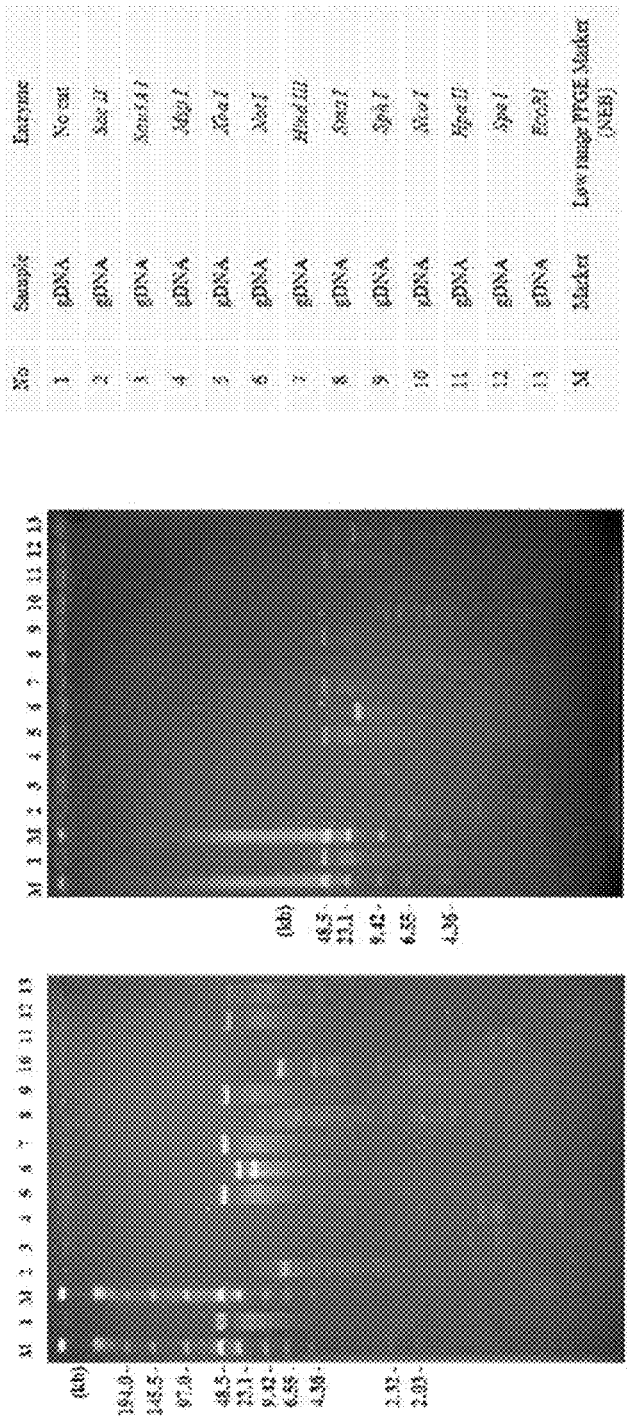
FIG. 11 shows the results of pulsed-field gel electrophoresis of the PAH1-C gDNA (Left) and PAH6-C gDNA (Right), and their digestions by 12 restriction endonucleases. Lane M indicates the low-range PFG marker (New England Biolabs). Lane 1 represents the phage gDNA without digestion. Lanes 2 to 13 represent digestion patterns of the phage PAH1-C and the PAH6-C produced by SacII, Sau3AI, MspI, XbaI, NotI, HindIII, SmaI, SphI, NcoI, HpaII, SpeI and EcoRI (New England Biolabs), respectively. The genome sizes of the two phage gDNAs were estimated as approximately 50 kb.

In general, Myoviridae phages are known to possess double-strand (ds) DNA genomes. Likewise, the gDNAs of PAH1-C and PAH6-C were completely digested by DNase I but not by RNase A or Mung bean nuclease. Thus, they were presumed to be ds DNA. In addition, the gDNAs were digested by SacII, Sau3AI, MspI, SmaI, NcoI, HpaII and EcoRI, and their size was estimated as approximately 50 kb (FIG. 11).

2) Morphological Classification of Isolated Phage

Figure 12:
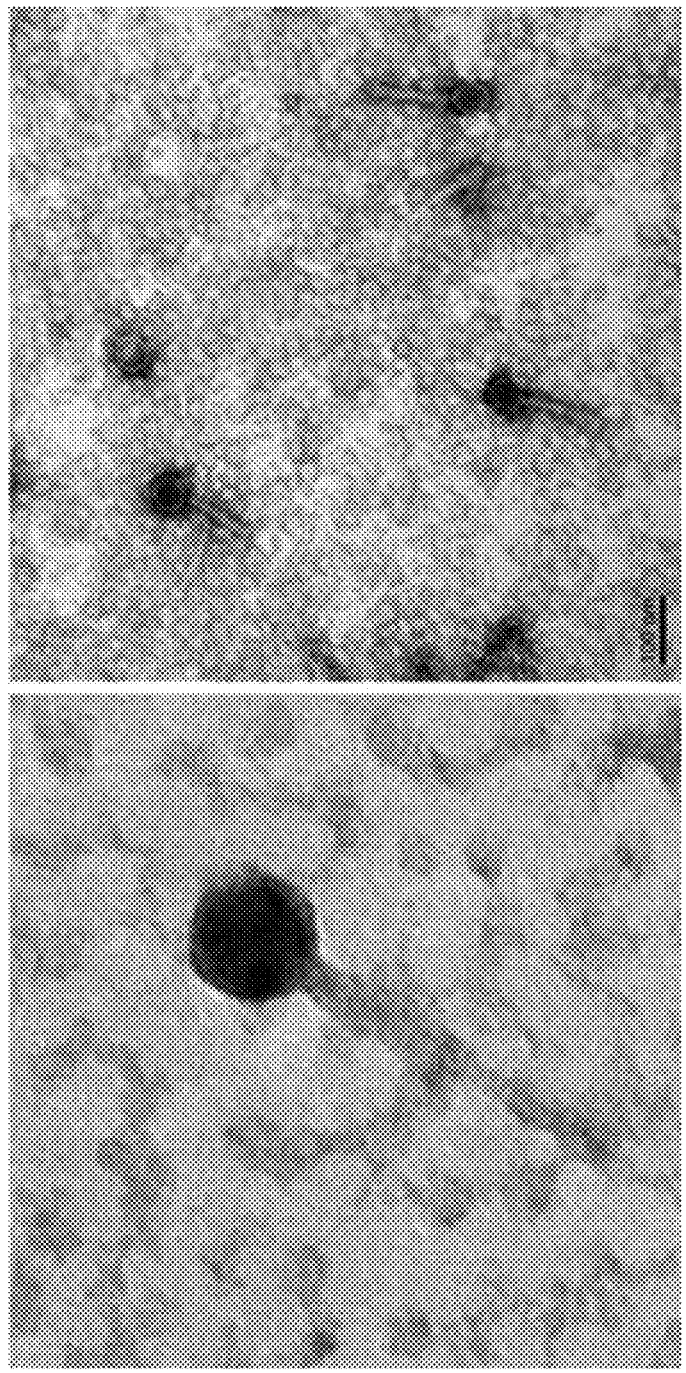
FIG. 12 is the results of observing the negatively stained PAH1-C (Left) or PAH6-C (Right) using an electron microscope.

The PAH1-C and PAH6-C were morphologically classified into the family Myoviridae and the order Caudovirales (FIG. 12), according to the classification of Ackermann. The tail length and width were 113±6/124±6 nm (mean±SD) (n=10) and 14±3/18±1 nm (n=10), respectively, and the head diameter was 41±3/63±3 nm (n=10).

Examination of Effect of PAH1-C and PAH6-C Against *Aeromonas hydrophila*

1) Host Cell Lysis Test

Figure 13:
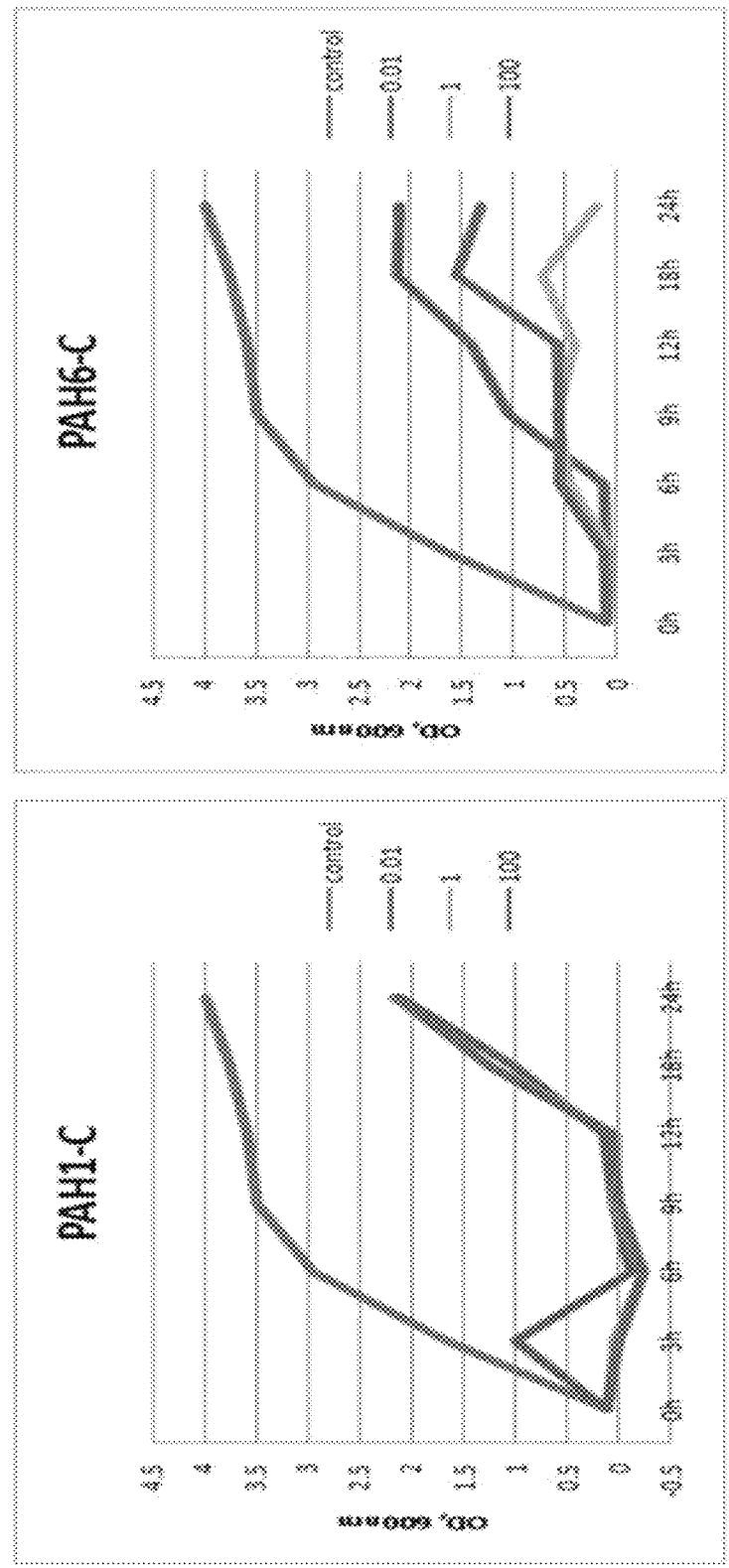
FIG. 13 shows the bacteriolytic activities of the PAH1-C and the PAH6-C against *Aeromonas hydrophila* AH16, which were co-cultured with the PAH1-C and the PAH6-C at MOI (multiplicity of infection) of 0.01, 1 and 100, respectively. The results show means±standard deviations from triplicate experiments.

The bacteriolytic activities of PAH1-C and PAH6-C were tested on culture of *Aeromonas hydrophila* AH16 (FIG. 13).

When the culture of *Aeromonas hydrophila* AH16 were not infected by PAH1-C and PAH6-C (control), the OD600 value continued to increase during the incubations. In contrast, viability of *Aeromonas hydrophila* AH16 was apparently retarded at MOI 0.01, 1 and 100 until 24 hrs after PAH1-C and PAH6-C infections.

2) Result of Examination of Treatment Effect of Phage Against Test Fish Artificially Infected with *Aeromonas hydrophila*

Figure 14:
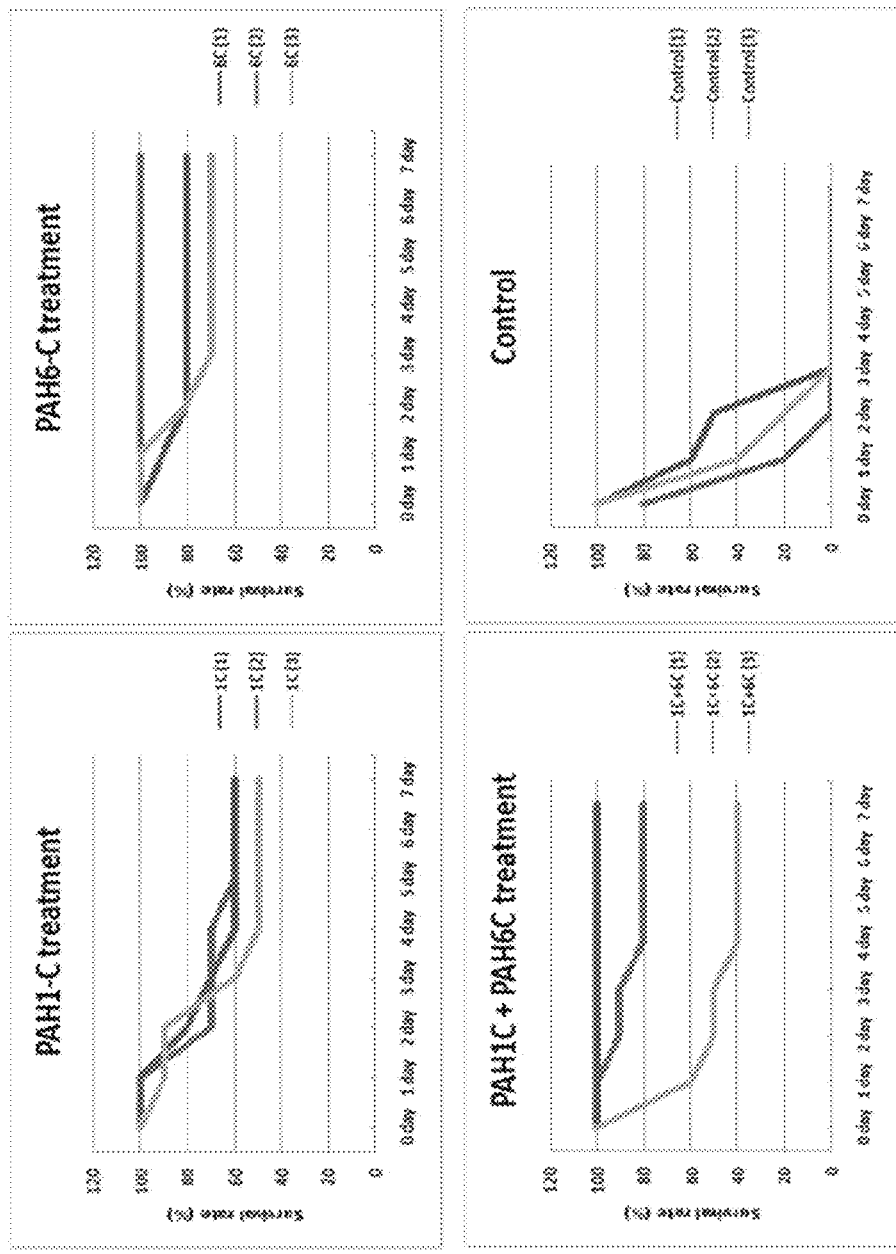
FIG. 14 shows therapeutic effects of the PAH1-C and PAH6-C phages against *Aeromonas hydrophila* infection of loach.

In the group inoculated with only *Aeromonas hydrophila* AH16, all fishes died within 3 days, and in the group treated with PAH1-C and PAH6-C, delayed death and reduced death rate were observed. In addition, it was found that the PAH6-C had better effect on inhibiting *Aeromonas hydrophila* infectious disease than the PAH1-C (FIG. 14).

The present disclosure has been described in detail. However, it should be understood that the detailed description and specific examples, while indicating preferred embodiments of the disclosure, are given by way of illustration only, since various changes and modifications within the spirit and scope of the disclosure will become apparent to those skilled in the art from this detailed description.

What is claimed is:

1. A composition comprising a surfactant and a dried bacteriophage comprising Caudovirales siphoviridae KCTC 12130BP, wherein said composition is formulated in a solid form.

2. The composition of claim 1, wherein said Caudovirales siphoviridae KCTC 12130BP is obtained from a culture.

3. A feed additive for fish and shellfish comprising isolated Caudovirales siphoviridae KCTC 12130BP or culture media comprising Caudovirales siphoviridae KCTC 12130BP, as an active ingredient; and carriers comprising a surfactant or/and an extender, wherein said feed additive is formulated in a solution.

4. An antibiotic comprising isolated Caudovirales siphoviridae KCTC 12130BP or culture media comprising Caudovirales siphoviridae KCTC 12130BP, as an active ingredient; and carriers comprising a surfactant or/and an extender, wherein said antibiotic is formulated in a solution.

5. An antiseptic comprising Caudovirales siphoviridae KCTC 12130BP or culture media comprising Caudovirales siphoviridae KCTC 12130BP, as an active ingredient; and carriers comprising a surfactant or/and an extender, wherein said antiseptic is formulated in a solution.

* * * * *